US011045501B2

(12) United States Patent
Ekre et al.

(10) Patent No.: US 11,045,501 B2
(45) Date of Patent: Jun. 29, 2021

(54) AUTOLOGOUS FECAL SAMPLE FOR USE IN THE TREATMENT OF MICROBIAL DYSBIOSIS

(71) Applicant: PLEONOVA AB, Stockholm (SE)

(72) Inventors: Hans Peter Torsten Ekre, Stockholm (SE); Lars Georg Engstrand, Stockholm (SE); Ola Gosta Flink, Stockholm (SE); Otto Sten Gunnar Skolling, Taby (SE)

(73) Assignee: BACTAVIVA AB, Stockholm (SE)

( * ) Notice: Subject to any disclaimer, the term of this patent is extended or adjusted under 35 U.S.C. 154(b) by 0 days.

(21) Appl. No.: 16/478,690

(22) PCT Filed: Jan. 19, 2018

(86) PCT No.: PCT/EP2018/051326
§ 371 (c)(1),
(2) Date: Jul. 17, 2019

(87) PCT Pub. No.: WO2018/134361
PCT Pub. Date: Jul. 26, 2018

(65) Prior Publication Data
US 2020/0046777 A1 Feb. 13, 2020

(30) Foreign Application Priority Data
Jan. 19, 2017 (EP) .................................... 17152248

(51) Int. Cl.
*A61K 36/00* (2006.01)
*A61K 35/37* (2015.01)
*A61P 31/04* (2006.01)
*A61K 9/00* (2006.01)

(52) U.S. Cl.
CPC ............ *A61K 35/37* (2013.01); *A61K 9/0053* (2013.01); *A61P 31/04* (2018.01)

(58) Field of Classification Search
None
See application file for complete search history.

(56) References Cited

U.S. PATENT DOCUMENTS

| 2014/0294774 A1* | 10/2014 | Nieuwdorp ................ A61P 3/04 424/93.4 |
| 2016/0207969 A1* | 7/2016 | Lee ........................... C07K 7/08 |
| 2016/0243175 A1 | 8/2016 | Bushman et al. |
| 2016/0354414 A1 | 12/2016 | Lee et al. |

FOREIGN PATENT DOCUMENTS

| WO | WO 2012/016287 | 2/2012 |
| WO | WO 2014/190229 | 11/2014 |

OTHER PUBLICATIONS

Borody et al., "Treatment of ulcerative colitis using fecal bacteriotherapy", Journal of Clinical Gastroenterol, 37(1):42-47 (Jan. 2003).
Borody et al., "Bacteriotherapy Using Fecal Flora", Journal of Clinical Gastroenterol, 38(6):475-483 (Jul. 2004).
Caballero et al., "Distinct but Spatially Overlapping Intestinal Niches for Vancomycin-Resistant Eneterococcus faecium and Cabapanem-Resistant Klebsiella pneumoniae"; PLoS Pathog. 11(9):e1005132 (2015).
Caporaso et al., "QIIME allows analysis of PC high-throughput community sequencing data" Nat. Methods 7(5):335-6 (2010).
Costello et al., "Fecal microbiota transplant for recurrent Clostridium difficile infection using long-term frozen stool is effective: clinical efficacy and bacterial viability data" Aliment Pharmacol Ther 42(8):1011-8 (Oct. 2015).
Donskey, "The role of the intestinal tract as a reservoir and source for transmission of nosocomial pathogens"; Clin Infect Dis 39(2):219-26 (Jul. 2004).
Hensgens et al., "All-cause and disease-specific mortiality in hospitalized patients with Clostridium difficile infection: a multicenter cohort study"; Clin Infect Dis 56(8):1108-16 (Apr. 2013).
Jones & Jones, "Does the Donor Matter? Donor vs. Patient Effects in the Outcome of Next-Generation Fecal Transplant for Recurrent Clostridium difficile Infection" Gastroenterology, 148(4; Suppl 1):S328-S329, Abstract 46th Annual Digestive Disease Week (DDW); May 16-19, 2015 (Apr. 2015).
Kelly et al., "Fecal microbiota transplant for treatment of Clostridium difficile infection in immunocompromised patients" Am J Gastroenterol 109(7):1065-71 (Jul. 2014).
Kelly et al., "Update on fecal microbiota transplantation 2015: Indications, Methodologies, Mechanisms, and Outlook", Gastroenterology, 149(1):223-237 (Jul. 2015).
Kleger et al., "Fecal transplant in refractory Clostridium difficile colitis"; Deutsches Arzteblatt International Feb. 2013, 110(7):108-115 (Feb. 2013).
Rossen et al., "Findings from a randomized controlled trial of fecal transplantation for patients with Ulcerative Colitis", Gastroenterology, 149(1):110-118.e4 (Jul. 2015).
Youngster et al., "Fecal microbiota transplant for relapsing Clostridium difficile infection using a frozen inoculum from unrelated donors: a randomized, open-label, controlled pilot study"; Clin Infect Dis 58(11):1515-22 (Jun. 2014).
Youngster et al., "Oral, frozen fecal microbiota transplant (FMT) capsules for recurrent Clostridium difficile infection"; BMC Med 14(1):134 (Sep. 2016).
Bartlett et al., "Clinical Practice. Antibiotic-associated diarrhea" N Engl J Med 346(5):334-9 (2002).

(Continued)

*Primary Examiner* — Qiuwen Mi
(74) *Attorney, Agent, or Firm* — McDonnell Boehnen Hulbert & Berghoff LLP

(57) ABSTRACT

The present disclosure relates to the use of autologous fecal samples obtained from a subject for use in prevention and/or treatment of microbial dysbiosis in the gastrointestinal tract in said subject and to related pharmaceutical compositions for oral administration. The disclosed autologous fecal samples are useful for treatment of microbial dysbiosis in the gastrointestinal tract associated with medical treatment and/or various indications, including chronic disease and infectious disease, for example *Clostridium difficile* infection.

13 Claims, No Drawings

(56) References Cited

OTHER PUBLICATIONS

Blot et al., "Colonization status and appropriate antibiotic therapy for nosocomial bacteremia caused by antibiotic-resistant gram-negative bacteria in an intensive care unit"; Infect Control Hosp Epidemiol 26(6):575-9 (2005).

Garey et al., "Meta-analysis to assess risk factors for recurrent Clostridium difficile infection"; J Hosp Infect. 70(4):298-304 (Dec. 2008).

Lee et al., "Frozen vs fresh fecal microbiota transplantation and clinical resolution of diarrhea in patients with recurrent Clostridium difficile infection" JAMA 315(2):142-9 (Jan. 2016).

Lessa et al., "Burden of Clostridium difficile infection in the United States"; N Engl J Med 372(9):825-34 (Feb. 2015).

Mäkitalo et al. Clostridium difficile rapport Available at: http://www.folkhalsomyndigheten.se/amnesomraden/statistik-och-undersokningar/sjukdomsstatistik/Clostridium-difficile-infektion/. Accessed Jan. 26, 2016, pp. 1-7 (submitted with English machine translation).

Pepin et al., "Outcomes of Clostridium difficile-associated disease treated with metronidazole or vancomycin before and after the emergence of NAP1/027"; Am J Gastroenterol 102(12):2781-8 (Dec. 2007).—Abstract submited.

Trotti et al., "CTCAE v3.0: development of a comprehensive grading system for the adverse effects of cancer treatment"; Semin Radiat Oncol. 13(3): 176-81 (Jul. 2003).

Van Nood et al., "Duodenal infusion of donor feces for recurrent Clostridium difficile"; N Engl J Med 368(5):407-415 (Jan. 2013).

Vardakas et al., "Treatment failure and recurrent of Clostridium difficile infection following treatment with vancomycin or metronidazole: a systematic review of the evidence" Int. J Antimicrob Agents 40(1):1-8 (Jul. 2012).

Yougnster et al., "Oral, capsulized, frozen fecal microbiota transplantation for relapsing Clostridium difficle infection"; JAMA 312(7)1772-8 (Nov. 2014).

\* cited by examiner

AUTOLOGOUS FECAL SAMPLE FOR USE IN THE TREATMENT OF MICROBIAL DYSBIOSIS

CROSS-REFERENCE TO RELATED APPLICATION

This application is a U.S. national stage application under 35 U.S.C. § 371 of International Application No. PCT/EP2018/051326, filed Jan. 19, 2018, which claims priority to European Patent Application No. 17152248.5, filed Jan. 19, 2017, all of which are explicitly incorporated by reference herein in their entirety.

FIELD OF THE INVENTION

The present disclosure relates to the use of autologous fecal samples obtained from a subject for use in prevention and/or treatment of microbial dysbiosis in the gastrointestinal tract in said subject and related pharmaceutical compositions for oral administration. The disclosed autologous fecal samples are useful for treatment of microbial dysbiosis in the gastrointestinal tract associated with various indications, including chronic disease and infectious disease, for example *Clostridium difficile* infection.

BACKGROUND

It is known that the human microbiome is important in health and disease. However, most of the mechanisms by which the microbiome mediates health and/or protection from disease are poorly understood. Certain chronic diseases have been shown to exhibit changes in the composition of the gastrointestinal microbiota, for example disturbances have been reported in patients with ulcerative colitis and inflammatory bowel disease. Disturbances of the intestinal microbiota may be caused by medical treatment, such as treatment of cancer with cytostatic drugs as well as treatment of infections with antibiotic treatment or treatment with drugs that suppress the immune system. Such treatment can lead to increase of growth of pathogenic opportunists leading to severe disease states. An example of this type of pathogen is *Clostridium difficile*.

*Clostridium difficile* is a toxin-producing bacterium and an opportunistic pathogen that causes diarrhea and colitis. *Clostridium difficile* infection (CDI) is a common and increasingly severe, primarily nosocomial infectious disease associated with a 2.5 fold increased 30 day mortality. In the US there were an estimated 453 000 cases and 29 300 deaths in 2011 due to CDI. Swedish laboratories reported ~9575 episodes of CDI in Sweden in 2015. CDI usually occurs following antibiotic mediated disruption of the normal intestinal microbiota. Other risk factors for CDI include hospital admission, advancing age, severe underlying disease and suppressed immunity.

A first episode of CDI is usually treated with metronidazole or vancomycin for 10 days. However, CDI recurs in up to 30% of patients after a first episode and in up to 60% after two or more recurrences (Vardakas K Z et al., Int J Antimicrob Agents 2012; 40(1): 1-8). The concept of treating CDI with additional antibiotics has recently been challenged by treatments reconstituting the gut flora. Fecal microbiota transplantation and vancomycin treatment cured 81-94% and 23-31% of patients, respectively in a ground breaking randomized clinical trial in patients with recurrent CDI (van Nood E et al., N Engl J Med 2013; 368(5): 407-15). The effectiveness of inoculating microbiota for treatment of recurrent CDI has since been confirmed (Costello S P et al., Aliment Pharmacol Ther 2015; 42(8): 1011-8; Kelly C R et al., Am J Gastroenterol 2014; 109(7): 1065-71; Lee C H et al., Jama 2016; 315(2): 142-9; and Youngster I et al., Jama 2014; 312(17): 1772-8).

In essence fecal microbiota transplantation results in reconstitution of the normal intestinal microbiota by inoculation of a healthy individual's microbiota into the diseased gut. For fecal microbiota transplantation, a suitable relative is typically found and screened for various infectious entities. A fresh stool sample is collected from the donor, mixed with saline, filtered and then introduced to the patient's intestine through a rectal enema, colonoscopy, nasogastric tube or gastroscopy. Identifying and screening takes days, enemas require bowel lavage and that diarrhea has been suppressed, obtaining a gastroscopy often takes time and there is a risk of regurgitation. The process thus takes time, is performed in a hospital, is costly, potentially disgusting and often associated with adverse side effects, such as nausea, vomiting and diarrhea.

Recent studies have shown that stools from unrelated healthy donors are as effective as stools from related donors (Youngster I et al., Clin Infect Dis 2014; 58(11): 1515-22). Frozen stools are as effective as fresh and a preliminary feasibility study found that oral, capsulized frozen fecal microbiota transplantation cured 90% (18/20) patients with recurrent CDI (Lee C H et al., Jama 2016; 315(2): 142-9; and Youngster I et al., Jama 2014; 312(17): 1772-8).

Antibiotic mediated destruction of the intestinal microbiota results in loss of colonization resistance not only against *C. difficile*. Drug resistant bacteria can also expand resulting in dense colonization. This increases the risk of resistance transmission and of bacteria crossing the intestinal membranes (translocation) resulting in deep tissue and bloodstream infection (Blot S et al., Infect Control Hosp Epidemiol 2005; 26(6): 575-9; Caballero S et al., PLoS Pathog 2015; 11(9): e1005132; and Donskey C J et al., Clin Infect Dis 2004; 39(2): 219-26).

Thus, there is a need in the field to provide a safe, tolerable and effective way to provide fecal microbiota transplantation to subjects in need thereof, such as subjects suffering or at risk of suffering from microbial dysbiosis in the gastrointestinal tract.

DESCRIPTION OF THE INVENTION

It is an object of the present disclosure to provide a safe, tolerable and effective therapeutic treatment and/or prophylactic treatment for subjects who are suffering or are at risk of suffering from microbial dysbiosis in the gastrointestinal tract.

It is an object of the present disclosure to provide therapeutic treatment and/or prophylactic treatment which decreases the resistance transmission via fecal microbial transplants.

It is an object of the present disclosure to provide therapeutic treatment and/or prophylactic treatment which decreases the risk of developing adverse side effects.

It is an object of the present disclosure to provide a therapeutic treatment and/or prophylactic treatment which is convenient for the subject, and that does not require hospital procedures or hospital monitoring for preparation of sample to be administered or for administration thereof. In particular, it is an object of the present invention to provide prophylactic treatment which prevents the occurrence or the recurrence of microbial dysbiosis in the gastrointestinal tract.

These and other objects, which are evident to the skilled person from the present disclosure, are met by different aspects of the invention as claimed in the appended claims and as generally disclosed herein.

Thus, in a first aspect of the present disclosure there is provided an autologous fecal sample, obtained from a subject and comprising at least one desired species of live microorganisms, for use in the prevention and/or treatment of microbial dysbiosis in the gastrointestinal tract in said subject, wherein said use comprises oral 1-10 times oral administration events per day during 1-30 days.

The present inventors have recognized the benefits of administering autologous fecal samples to a subject in need thereof which circumvents the need for extensive screening and reduces or eliminates the risk that said subject will be infected with unwanted pathogens, such as pathogens derived from a donor. Additionally, subjects at risk if developing an infectious disease, for example due to bacterial, viral, fungal or parasitic infection, can be identified prior to the potential pathogen exposure. For example, subjects at high risk of developing *C. difficile* infection or other infections can be identified prior to planned medical procedures that further increase the risk of infection. Also, subjects who are at risk of developing infectious disease due to travel associated pathogen exposure are envisioned to benefit from the present invention. The inventive concept disclosed herein allows such subjects to store fecal material for future autologous microbiota inoculation. Additionally, subjects who suffer from chronical diseases influencing the gastrointestinal microbiota may benefit from autologous fecal samples, which samples were obtained from said subjects during periods of disease remission. Additionally, the administration of an autologous as compared to an allogenic fecal sample is expected to reduce the risk of developing adverse side effects, including fever, gastrointestinal symptoms, nausea, diarrhea, vomiting, headache, fatigue, and rash, in particular gastrointestinal symptoms such as nausea, diarrhea and vomiting.

Importantly, samples can be obtained and stored in advance, and therefore be available immediately for administration when needed, for example due to clinical manifestations of disease symptoms or even before the clinically manifestation of disease symptoms.

As used herein, the terms "subject" and "patient" are used interchangeably.

It will be understood that said sample comprises at least one desired species of live bacteria, and may comprise many more such species and other microorganisms, such as fungi, viruses and parasites. As used herein, the term "desired species" refers to microorganism species which normally inhabit the gastrointestinal tract, thus makes up part of the gastrointestinal microbiota. It will be appreciated that said at least one desired species may be different between different individuals as the gastrointestinal microbiota differs between different individuals and that said at least one desired species is at least one species present in the gastrointestinal tract of the specific subject while in a healthy condition or in a state of remission as explained herein. The gastrointestinal microbiota is the complex community of microorganisms that live in the digestive tracts of humans and other animals exhibiting both commensal and mutualistic relationships with the host.

In one embodiment there is provided an autologous fecal sample for use as described herein, wherein said at least one desired species of live microorganisms is present in the gastrointestinal tract of said subject when in a healthy condition or in a state of remission. In another embodiment, there is provided an autologous fecal sample for use as described herein, wherein said sample is obtained from said subject while in said healthy condition or said state of remission.

As used herein, the term "live bacteria" includes both actively growing bacteria and bacterial spores. A bacterial spore is a structure produced by bacteria that is resistant to many environmental or induced factors to which the bacteria may be subjected. When a bacterium is starving or senses environmental change, for example extreme temperatures and drought, it will produce a spore. This spore is a protective, thick cell wall and can help the bacteria survive for several years by living in a dormant state. When environmental conditions improve, the spore will break and the bacteria will resume active growth. Thus, in one embodiment said sample comprises live bacteria. In one embodiment, said sample comprises both actively growing bacteria and bacterial spores. In another embodiment, said sample comprises actively growing bacteria and does essentially not contain bacterial spores. In another embodiment, said sample comprises bacterial spores and does essentially not contain actively growing bacteria.

The human gastrointestinal microbiota has the largest numbers of bacteria and the greatest number of species compared to other areas of the body. The gastrointestinal microbiota is established one to two years after birth, and by that time the intestinal epithelium and the intestinal mucosal barrier that it secretes have co-developed in a way that is tolerant to, and even supportive of, the gastrointestinal microbiota and that also provides a barrier to pathogenic organisms. The composition of the microbiota of the gastrointestinal tract varies along the tract (at longitudinal levels) and across the tract (at horizontal levels) where certain bacteria attach to the gastrointestinal epithelium and others occur in the lumen. In the stomach and small intestine, relatively few species of bacteria are generally present. The colon, in contrast, contains up to $10^{14}$ cells per gram of intestinal content. These bacteria represent between 300 and 1000 different species. However, 99% of the bacteria come from about 30 or 40 species. As a consequence of their abundance in the intestine, bacteria also make up to 60% of the dry mass of feces.

As used herein, the terms "microorganism" and "microbe" encompasses bacteria (including anaerobic and aerobic bacteria), viruses, parasites and fungi. Thus, the terms "microbial flora" and "microbiota" refers to the flora of bacteria (including anaerobic and aerobic bacteria), viruses, parasites and fungi.

It will be appreciated that in some embodiments there is provided the autologous fecal sample for use as disclosed herein, wherein said sample comprising at least one desired species of live microorganisms comprises the diversity of live microorganisms present in the gastrointestinal tract of said subject, such the unselected diversity of live microorganisms present in the gastrointestinal tract of said subject. As used herein, the term "diversity of live microorganisms" refers to the population of live microorganisms which is present in the gastrointestinal tract of said subject, which population may comprise different species, gena and phyla of microorganisms. In some embodiments, said microorganisms are bacteria. As used herein, the term "unselected diversity" refers to true diversity of the population of live microorganisms which is present in the gastrointestinal tract, thus is the diversity of the gastrointestinal tract, which population has not been subjected to any process or method to selectively increase or decrease any subset of said population. For clarity, in the context of the present disclosure the autologous fecal sample comprising the unselected diversity of live microorganisms present in the gastrointestinal tract is an autologous fecal sample comprising a population of live microorganisms, which population has not been subjected to any process or method to selectively increase or decrease any subset of said population. Such a sample is considered to represent the microbiota of the gastrointestinal tract in terms of species, gena and phyla of microorganisms and as well as populations distribution. Importantly, it will be appreciated that said diversity may differ between different subjects, for example due to genetic, health, dietary and/or environmental factors. Hence, two subjects may exhibit different microbial diversity in the gastrointestinal tract, such as different diversity of live microorganisms in the gastrointestinal tract, such as different diversity of live bacteria in the gastrointestinal tract. Thus, in one embodiment said diversity is specific to said subject.

The four dominant bacterial phyla in the human gut are Firmicutes, Bacteroidetes, Actinobacteria, and Proteobacteria. Most bacteria belong to the genera *Bacteroides, Clostridium, Fecalibacterium, Eubacterium, Ruminococcus, Peptococcus, Peptostreptococcus*, and *Bifidobacterium*. Other genera, such as *Escherichia* and *Lactobacillus*, are present to a lesser extent. Fungal genera that have been detected in the gastrointestinal tract include *Candida, Saccharomyces, Aspergillus, Penicillium, Rhodotorula, Trametes, Pleospora, Sclerotinia, Bullera*, and *Galactomyces*. Archaea constitute another large class of gut flora which are important in the metabolism of the bacterial products of fermentation.

Thus, in one embodiment as disclosed herein, the diversity of live microorganisms comprises bacteria from at least one, such as at least two, such as at least three, such as four, of the phyla Firmicutes, Bacteroidetes, Actinobacteria and Proteobacteria. In another embodiment, said diversity of live microorganisms comprises bacteria from at least one, such as at least two, such as at least three, such as at least four, such as at least five, such as at least six, such as at least seven, such as eight, of the genera *Bacteroides, Clostridium, Fecalibacterium, Eubacterium, Ruminococcus, Peptococcus, Peptostreptococcus*, and *Bifidobacterium*.

Thus, in one embodiment as disclosed herein, said at least one desired species of live bacteria is one, two, three, four or more species of live bacteria selected from the group consisting of the phyla Firmicutes, Bacteroidetes, Actinobacteria and Proteobacteria. For example, said at least one desired species of live bacteria may be from the same of different phyla. In another embodiment, said at least one desired species of live bacteria is one, two, three, four, five, six, seven, eight or more species of live bacteria selected from the group consisting of the genera *Bacteroides, Clostridium, Fecalibacterium, Eubacterium, Ruminococcus, Peptococcus, Peptostreptococcus*, and *Bifidobacterium*. For example, the at least two or more desired species of live bacteria may be from the same of different genera mentioned above.

In the stomach, the gastrointestinal microbiota includes *Streptococcus, Staphylococcus, Lactobacillus, Peptostreptococcus*, and types of yeast, which are species that can survive in acidic environment in the stomach. Gram positive cocci and rod shaped bacteria are the predominant microorganisms found in the small intestine, which exhibits low levels of microorganisms due to proximity to the stomach. However, in the distal portion of the small intestine alkaline conditions support gram-positive bacteria of the Enterobacteriaceae.

Bacteria make up most of the flora in the colon and 60% of the dry mass of feces. It is estimated that somewhere between 300 and 1000 different species live in the gut, with most estimates at about 500. 99% of the bacteria is estimated come from about 30 or 40 species, with *Fecalibacterium prausnitzii* being the most common species in healthy adults. Non-limiting examples of bacterial species found in the human colon are *Bacteroides fragilis, Bacteroides melaninogenicus, Bacteroides oralis, Enterococcus fecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enteritidis, Fecalibacterium prausnitzii, Peptostreptococcus* sp. and *Peptococcus* sp. Thus, in one embodiment said at least one desired species of live bacteria is selected from the group consisting of *Bacteroides fragilis, Bacteroides melaninogenicus, Bacteroides oralis, Enterococcus fecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enteritidis, Fecalibacterium prausnitzii, Peptostreptococcus* sp. and *Peptococcus* sp.

The gastrointestinal microbiota has been reported to be involved in synthesis and excretion of vitamins, prevention of colonization by pathogens, antagonization of other bacteria for example by means of bacterial toxins, metabolism and stimulation of the development of certain tissues.

The skilled person is aware that certain diseases have been shown to exhibit changes in the composition of the gastrointestinal microbiota, such as the decrease in the diversity of the microbiome with low levels of fecal Lactobacilli and Bifidobacteria, high levels of facultative anaerobic bacteria such as *Escherichia coli*, and increased ratios of Firmicutes:Bacteroidetes in subjects with irritable bowel syndrome; the domination of Proteobacteria and Actinobacteria in subjects with ulcerative colitis; and the over-representation of *Enterococcus faecium* and several Proteobacteria in subjects with Crohn's disease. Additionally, disruption of the gastrointestinal microbiota, for example due to antibiotic use, allows competing opportunistic microorganisms like *Clostridium difficile* to become established. The growth of opportunistic microorganisms, such as *C. difficile*, is normally held in check by other members of the microbiota. When antibiotics given for other infections cause collateral damage to the normal microbiota of the gastrointestinal tract, opportunistic microorganisms may be able to expand and grow. In the case of *C. difficile* this leads to a serious diarrheal syndrome called pseudomembranous colitis.

As used herein, the term "microbial dysbiosis in the gastrointestinal tract" refers to a disturbed microbial flora or microbiota in said tract. For example, microbial dysbiosis may be characterized by that normally dominating species are underrepresented and normally outcompeted or contained species are overrepresented, such as for example *C. difficile*. Microbial dysbiosis in the gastrointestinal tract has been reported to be associated with diseases, such as inflammatory bowel disease, obesity, cancer, and colitis and other. The skilled person is aware of the meaning of microbial dysbiosis in the gastrointestinal tract in the present context.

As used herein the term "administration event" refers to the individual administration of the autologous fecal sample as disclosed herein. Thus, each individual dose administered is considered an individual administration event. For example, the administration of 2 consecutive doses during a period of 5 minutes is considered as two individual administration events. For example, the administration of 2 consecutive doses performed once in the morning and once in the evening of the same day are considered as four administrations events at two occasions.

In one embodiment of the first aspect, there is provided an autologous fecal sample for use as disclosed herein, wherein the said sample is obtained from said subject while in said healthy condition. It is considered that the fecal sample obtained during a healthy condition will contain the desired microorganisms, for example bacteria, in sufficient amounts.

As used herein, the term "healthy condition" refers to a healthy condition in terms of the microbiota of the gastrointestinal tract, such as a state which is free from or exhibits minor microbial dysbiosis. It will be appreciated that the term "healthy condition" also includes conditions which are free from symptoms associated with microbial dysbiosis. Additionally, the term "healthy condition" refers to conditions wherein the microbiota of the gastrointestinal tract is not effected by medical treatment, such as for example antibiotic treatment or other drug treatment. To clarify, the sample may be obtained from a subject when said subject is healthy or asymptomatic in terms of microbial dysbiosis. It will be appreciated that said sample may also be obtained from said subject while the subject manifests gastrointestinally unrelated clinical symptoms, for examples clinical symptoms which manifest in body parts or tissues which are not the gastrointestinal tract. Additionally, in the present context, a subject in a healthy condition also includes subjects exhibiting clinical symptoms in the gastrointestinal tract, which symptoms are not related to the microbiota.

In one embodiment of the first aspect, there is provided an autologous fecal sample for use as disclosed herein, wherein said subject suffers from a chronic disease and said at least one desired species of live microorganisms is present in the subject when in a state of remission. As discussed above, some chronic diseases have been reported to show microbial dysbiosis of the gastrointestinal tract. It may be beneficial to administer to a subject suffering from such chronic disease, for example during a flare up or active stage of the chronic disease which manifests clinical symptoms, an autologous fecal sample which was obtained from the subject during a stage of remission, such as symptom-free remission or remission with low grade symptoms. It is considered that the fecal sample obtained during symptom-free remission or remission with low grade symptoms will contain the desirable microorganisms in sufficient amounts.

Thus, in one embodiment, said autologous fecal sample is obtained from said subject while the subject is in a healthy state or in a state of remission. It will be appreciated that said autologous fecal sample as disclosed herein may be administered also to healthy individuals as it carries no risk for transmission of foreign (non-autologous) infections, non-autologous resistance transmission or foreign (non-autologous) intestine tissue fragments or the like.

It is considered that sufficient amounts of desirable microorganisms, for example bacteria, as mentioned above are sufficient to reconstitute the normal microbiota of the gastrointestinal tract. In one embodiment, there is provided an autologous fecal sample for use as disclosed herein, wherein said prevention and/or treatment comprises autologous reconstitution of normal microbiota of the gastrointestinal tract, such as the normal microbiota downstream of the duodenum. For clarity, the term "normal microbiota" as used herein refers to the microbiota of the subject when in a healthy state or in a state of remission. In particular, said reconstitution comprises repopulation of the gastrointestinal tract with desirable bacteria. In one embodiment, the autologous reconstitution comprises repopulation of the gastrointestinal tract with said at least one species of microorganism, such as at least one species of bacteria. In one embodiment, said repopulation is repopulation with at least 50% such as with at least 60%, such as at least with 70%, such as at least with 80%, such at least with 90% of the desired microorganism species, such as the desired bacterial species. In one embodiment, said repopulation is repopulation with at least 25% such as with at least 50%, such as at least with 75%, such as at least with 80%, such at least with 90% of the phyla and/or genera discussed previously.

As briefly discussed above, microbial dysbiosis may be due to medical treatment, for example immune system suppressant treatment which may allow for the development of microbial dysbiosis or antibiotic treatment which may allow for underrepresentation of certain microorganism species and overrepresentation of other microorganism species, such as underrepresentation of certain bacterial species and overrepresentation of other bacterial species.

In one embodiment, there is provided an autologous fecal sample for use as described herein, wherein said microbial dysbiosis is caused by medical treatment. Said microbial dysbiosis may be due to antibiotic treatment. Examples of such treatment include, but are not limited to treatment of *C. difficile* infections with metronidazole and/or vancomycin. Said microbial dysbiosis may be due to other medical treatments, such as medical treatments selected from the group consisting of immunosuppressive treatment; cytostatic treatment; radiation treatment; surgical treatment; treatment with biguanides, such as metformin; and other treatments affecting the microbiota of the gastrointestinal tract in a way leading to microbial dysbiosis. Thus, in one embodiment, said medical treatment is selected from the group consisting of antibiotic treatment; immunosuppressive treatment; cytostatic treatment; radiation treatment; surgical treatment; treatment with biguanides, such as metformin; and other treatments affecting the microbiota of the gastrointestinal tract in a way leading to microbial dysbiosis. It will be appreciated that said medical treatment may be an earlier medical treatment. A non-limiting example of such earlier medical treatment is antibiotic treatment. Alternatively, said medical treatment may be a concomitant medical treatment. It is envisioned that reconstitution of the microbiota can cure, lessen or alleviate adverse effect associated with an administered medical treatment. Therefore, said autologous fecal sample may be administered after and/or during said treatment. For example, it may be beneficial to administer the autologous fecal sample to a subject undergoing cytostatic treatment.

In one embodiment, there is provided an autologous fecal sample for use as disclosed herein, wherein said microbial dysbiosis is associated with a chronic disease affecting the gastrointestinal tract, such as a chronic disease selected from the group consisting of irritable bowel syndrome, Crohn's disease, ulcerative colitis, collagenous colitis and diverticulitis. The skilled person will appreciate that the disease listed above are non-limiting examples of chronic diseases affecting the gastrointestinal tract.

Also, said imbalance may be causes by an infectious disease. Non-limiting examples of infectious diseases include bacterial infections, such as an infection by *Clostridium, Salmonella*, EHEC, ETEC, *Klebsiella* or *Shigella*; viral infections, such as an infection by calicivirus or ROTA-virus; and parasitic infections, such as an infection by *Cryptosporidium* or *Giardia*. In another embodiment, said microbial dysbiosis is associated with an infectious disease affecting the gastrointestinal tract, such as a disease selected from the group consisting of diseases caused by a bacterial infection, such as an infection by *Clostridium*, *Salmonella*, EHEC, ETEC, *Klebsiella* or *Shigella*; a viral infection, such as an infection by calicivirus or ROTA-virus; and a parasitic infection, such as an infection by *Cryptosporidium* or *Giardia*. In one embodiment, said microbial dysbiosis is associated with a bacterial infection selected from the group consisting of infections by *Clostridium*, *Salmonella*, EHEC, ETEC, *Klebsiella* and *Shigella*. For example, said microbial dysbiosis may lead to that the subject manifests symptoms of diarrhea induced by medical treatment, such as antibiotic induced diarrhea or diarrhea induced by the infectious agent, such as *C. difficile* induced diarrhea. In particular, in one embodiment, said microbial dysbiosis is associated with a *Clostridium difficile* infection, such as an ongoing *Clostridium difficile* infection or an earlier *Clostridium difficile* infection. In one embodiment, there is provided an autologous fecal sample for use as disclosed herein, wherein the prevention and/or treatment is carried out post at least one *Clostridium difficile* infection. As *Clostridium difficile* infection recurs in up to 30% of subjects after a first episode and in up to 60% after two or more recurrences, it is desirable to prevent said recurrence. Thus, said prevention may be the prevention of occurrence or recurrence of a *Clostridium difficile* infection. Said prevention may be the prevention of *Clostridium difficile* translocation across the intestinal membrane.

It will be appreciated that it is also beneficial to prevent the first occurrence of a *Clostridium difficile* infection. In one embodiment, there is provided an autologous fecal sample for use as disclosed herein, wherein said *Clostridium difficile* infection is a first *Clostridium difficile* infection.

It is envisioned that a patient who undergoes and completes an antibiotic treatment, such as an antibiotic treatment targeting *Clostridium difficile* infection or another infection such as a *Salmonella*, EHEC, ETEC, *Klebsiella* and *Shigella* infection, is administered the autologous fecal sample as disclosed herein, in order to achieve reconstitution of the microbiota in the gastrointestinal tract and thus prevent the recurrence or reduce the risk of recurrence of said infection or the occurrence of a different infection. It is envisioned that the said administration will be beneficial already after the first infection episode, such as a first *Clostridium difficile* infection or another infection episode such as a *Salmonella*, EHEC, ETEC, *Klebsiella* and *Shigella* infection episode, in order to prevent recurrence of infection or occurrence of a different infection.

Thus, in one embodiment it is provided an autologous fecal sample for use as disclosed herein, wherein said administration begins at least 1 day, such as at least 2 days, such as 3 days or more, after the completion of the antibiotic treatment. In some embodiments, said administration begins within 1-5 days, such as 2-5 days, such as 2-4 days, such as 2-3 days or 1-4 days, such as 1-3 days, such as 1-2 days after the completion of the antibiotic treatment.

In one embodiment, it is provided an autologous fecal sample for use as disclosed herein, wherein a first administration event occurs at least 1 day, such as at least 2 days, such as 3 days or more, after the completion of the antibiotic treatment. In some embodiments, said administration occurs within 1-5 days, such as 2-5 days, such as 2-4 days, such as 2-3 or 1-4 days, such as 1-3 days, such as 1-2 days after the completion of the antibiotic treatment. For example, said first administration event occurs within 1-5 days, such as 2-5 days, such as 2-4 days, such as 2-3 days or 1-4 days, such as 1-3 days, such as 1-2 days after the completion of the metronidazole and/or vancomycin and/or fidaxomicin treatment.

Additionally, wherein there is a risk for developing a first *Clostridium difficile* infection, it may be beneficial to prevent such development. For example, this may be the case for a subject undergoing antibiotic treatment. Thus, in one embodiment, there is provided an autologous fecal sample for use as disclosed herein, wherein said *Clostridium difficile* infection is a first *Clostridium difficile* infection.

In one embodiment it is provided an autologous fecal sample for use as disclosed herein disclosed herein, wherein said administration begins at least 1 day, such as at least 2 days, such as 3 days or more, after the completion of the antibiotic treatment, which antibiotic treatment targets at least one different infectious agent than *Clostridium difficile*. In some embodiments, said administration begins within 1-5 days, such as 2-5 days, such as 2-4 days, such as 2-3 days or 1-4 days, such as 1-3 days, such as 1-2 days after the completion of an antibiotic treatment, which antibiotic treatment targets at least one different infectious agent than *Clostridium difficile*. For example, said antibiotic treatment may target an infectious agent selected from *Salmonella*, EHEC, ETEC, *Klebsiella* and *Shigella* or another bacterial strain. The skilled person appreciates that the above examples are non-limiting. In one embodiment, it is provided an autologous fecal sample for use as disclosed herein, wherein a first administration event occurs at least 1 day, such as at least 2 days, such as 3 days or more, after the completion of the antibiotic treatment, which antibiotic treatment targets at least one different infectious agent than *Clostridium difficile*. In some embodiments, said administration occurs within 1-5 days, such as 2-5 days, such as 2-4 days, such as 2-3 days or 1-4 days, such as 1-3 days, such as 1-2 days after the completion of the antibiotic treatment, which antibiotic treatment targets at least one different infectious agent than *Clostridium difficile*. In one embodiment, said antibiotic treatment is a broad spectrum antibiotic treatment.

It will be appreciated that it may be beneficial to administer the fecal sample as disclosed herein to a subject who is at risk of developing an infection caused by any of the above mentioned pathogens. For example, said risk may be due to exposure to said pathogen by being in contact with an infected site or infected individual as well as exposure to infected drinking liquids or foods. For example, such exposure may occur during travel. It will be appreciated that it may be beneficial to administer the fecal sample as disclosed herein to said subject to prevent or mitigate clinical symptoms.

As discussed above, the autologous fecal sample may be administered at 1-10 administration events a per day, wherein each administration event refers to the individual administration of a dose the autologous fecal sample as disclosed herein. Thus, each individual dose administered is considered an individual administration event. For example, administration of 2 doses at one occasion is considered to correspond to two administration events. To illustrate 9 administration events per day may correspond to administration of 3 doses at each of 3 occasions per day; 6 administration events per day may correspond to administration of 3 doses at each of 2 occasions per day or to administration of 2 doses at each of 3 occasions per day. It will be appreciated that fewer administration events is beneficial for subject compliance and convenience of treatment. Additionally, it is important that a subject experiences as little discomfort as possible during administration. Thus, in one embodiment there is provide an autologous fecal sample for use as disclosed herein, wherein said use comprises 1-10 administration events per day, such as 1-9 administration events per day, such as 1-8 administration events per day, such as 1-6 administration events per day, such as 2-6 administration events per day, such as 3-6 administration events per day or 2-4 times per day, such as 2, 3 or 4 administration events per day. In one embodiment, said use comprises 1, 2, 3, 4, 5, 6, 7, 8, 9 or 10 administration events per day.

In order to obtain high subject compliance, that is the degree to which a subject correctly follows medical advice, it is generally considered that the treatment regimens may not be complex in order to for a subject to be able to easily follow them. For example, it may be preferable that the administration of a drug is no more than on 5 separate occasions per day. In one embodiment, said administration is administration at 1, 2 or 3 separate occasions per day, such as 1 or 2 separate occasions per day. In one embodiment, said occasions are separated by at least 4 hours, such as at least 6 hours, such at least 8 hours or at least 12 hours. In one embodiment, 1, 2, 3, 4 or 5, such as 1, 2, 3, or 4 doses are administered at each said occasion. In one embodiment, 1, 2 or 3 doses are administered at each occasion, such as 1 or 2 doses at each occasion.

It will be appreciated that it may be beneficial that said administration is continued until a stable recolonization of the gastrointestinal microbiota is achieved. Thus, in one embodiment, there is provided an autologous fecal sample for use as described herein, wherein said administration is continued for a period of at least 5 days, such as for 5-30 days, such as 5-14 days, such as 5-10 day. In one embodiment, said administration is continued for 5-7 days, such as for 5 or 7 days, for example for 5, 6 or 7 days. In one embodiment, said administration is continued for 10 days. In one embodiment, said administration is continued for any of 5, 6, 7, 8, 9 or 10 days. In one embodiment, said administration is for 1-4 days, such as 1, 2, 3, or 4 days.

It will furthermore be appreciated that convenient administration routes are preferable and increase subject compliance. It will be appreciated that non-invasive administration may be generally preferable. For example, oral administration is considered a safe and easy administration route and can conveniently be used for administration in the comfort the subject's home environment or other environment of choice. It is furthermore considered beneficial that said administration can be performed without the assistance of and/or monitoring by health care professionals.

Thus, in one embodiment there is provided an autologous fecal sample for use as disclosed herein, wherein said administration is oral administration, such as oral self-administration, such as oral out-patient self-administration.

The skilled person will appreciate that the embodiments discussed above in relation to the first aspect of the present disclosure, are equally relevant and applicable to the second, third and further aspects disclosed herein. This particularly applies to embodiments relating to the composition/content and source of the fecal sample, the cause underlying microbial dysbiosis and to embodiments relating to the dose regime, as well as, where applicable, the mode and route of administration. For the sake of brevity these will not be repeated here or will only be briefly mentioned.

In a second aspect of the present disclosure, there is provided a pharmaceutical composition for oral administration comprising a therapeutically effective amount of an autologous fecal sample, obtained from a subject and comprising at least one desired species of live microorganisms, and at least one pharmaceutically acceptable excipient, for use in the prevention and/or treatment of microbial dysbiosis in the gastrointestinal tract of said subject, wherein said use comprises 1-10 administration events per day during 1-30 days. Said pharmaceutical composition comprises at least one pharmaceutically acceptable excipient or carrier. Non-limiting examples of excipients includes surfactants; anti-oxidants; cryo-protectants; vegetable oils; diluents; disinteragrans; binders: lubricants; glidants; and agents that modify release of the active agent, such as polymers; for example such as surfactants, anti-oxidants and cryo-protectants. The skilled person is aware of suitable excipients and carriers.

In one embodiment, said at least one desired species of live microorganism, such as live bacteria, is present in the gastrointestinal tract of said subject when in a healthy condition. In another embodiment, wherein said subject suffers from a chronic disease and said at least one desired species of live microorganism, such as live bacteria, is present in the gastrointestinal tract of said subject when in a state of remission.

In one embodiment, the pharmaceutical compositions as disclosed herein, comprises an autologous fecal sample obtained from said subject while in said healthy condition or said state of remission. In particular, said sample comprising least one desired species of live microorganism, such as live bacteria, may comprise the diversity of live microorganism, such as live bacteria, present in the gastrointestinal tract of said subject, such the unselected diversity of live microorganism, such as live bacteria, present in the gastrointestinal tract of said subject. Additionally, said diversity may be specific to said subject as discussed in the context of the first aspect.

In one embodiment, there is provided a pharmaceutical composition for use as disclosed herein, wherein said diversity of live microorganisms comprises bacteria from at least one, such as at least two, such as at least three, such as four, of the phyla Firmicutes, Bacteroidetes, Actinobacteria and Proteobacteria. In another embodiment, there is provided a pharmaceutical composition for use as disclosed herein, wherein said diversity of live microorganisms, comprises bacteria from at least one, such as at least two, such as at least three, such as at least four, such as at least five, such as at least six, such as at least seven, such as eight, of the genera *Bacteroides, Clostridium, Fecalibacterium, Eubacterium, Ruminococcus, Peptococcus, Peptostreptococcus*, and *Bifidobacterium*.

In one embodiment, said prevention and/or treatment comprises autologous reconstitution of normal microbiota of the gastrointestinal tract, such as the normal microbiota downstream of the duodenum. In particular, said autologous reconstitution comprises repopulation of the gastrointestinal tract with at least one desired species of microorganisms, such as bacteria. In particular, said reconstitution may comprise repopulation of the gastrointestinal tract with said at least one species of microorganisms, such as bacteria. In one embodiment, said repopulation is repopulation with at least 50% such as with at least 60%, such as at least with 70%, such as at least with 80%, such at least with 90% of the desired species of microorganisms, such as desired bacterial species. In one embodiment, said repopulation is repopulation with at least 25% such as with at least 50%, such as at least with 75%, such as at least with 80%, such at least with 90% of the phyla and/or genera discussed previously.

As discussed in connection with the first aspect as disclosed herein, said microbial dysbiosis may be a microbial dysbiosis caused by medical treatment, such as antibiotic treatment, or a microbial dysbiosis associated with a disease. Thus, in one embodiment, there is provided a pharmaceutical composition for use in treatment and/or prevention of microbial dysbiosis in the gastrointestinal tract, wherein said imbalance is caused by medical treatment. Said imbalance may be caused by antibiotic treatment or by other medical treatment, such as a medical treatment is selected from the group consisting of immunosuppressive treatment; cytostatic treatment; radiation treatment; surgical treatment; and treatment with biguanides, such as metformin. Said treatment may be an earlier treatment or a concomitant treatment as discussed above. In one embodiment, said microbial dysbiosis is associated with a chronic disease affecting the gastrointestinal tract, such as a chronic disease selected from the group consisting of irritable bowel syndrome, Crohn's disease, ulcerative colitis, collagenous colitis and diverticulitis. In one embodiment, said microbial dysbiosis is associated with an infectious disease affecting the gastrointestinal tract selected from the group consisting of disease caused by a bacterial infection, such as an infection by *Clostridium*, *Salmonella*, EHEC, ETEC, *Klebsiella* or *Shigella*; a viral infection, such as an infection by calicivirus or ROTA-virus; and a parasitic infection, such as an infection by *Crytosporidium* or *Giardia*. In one embodiment, said microbial dysbiosis is associated with a bacterial infection selected from the group consisting of infections by *Clostridium*, *Salmonella*, EHEC, ETEC, *Klebsiella* and *Shigella*.

In particular, there is provided a pharmaceutical composition for use as disclosed herein, wherein said microbial dysbiosis is associated with a *Clostridium difficile* infection, such as an ongoing *Clostridium difficile* infection or an earlier *Clostridium difficile* infection. In one embodiment, said prevention and/or treatment is carried out post at least one *Clostridium difficile* infection. For example, said prevention is the prevention of occurrence or recurrence of a *Clostridium difficile* infection. Furthermore, said prevention may be the prevention of *Clostridium difficile* translocation across the intestinal membrane.

In one embodiment, there is provided a pharmaceutical composition for use as disclosed herein, wherein said *Clostridium difficile* infection is a first *Clostridium difficile* infection.

In particular as discussed in detail in the context of the first aspect, it is envisioned that it is beneficial for a patient who undergoes and completes an antibiotic treatment, such as an antibiotic treatment targeting *Clostridium difficile* infection or another infection, is administered the pharmaceutical composition as disclosed herein, in order to achieve reconstitution of the microbiota in the gastrointestinal tract and thus prevent the recurrence or reduce the risk of recurrence of said infection or the occurrence of a different infection. It is envisioned that said administration is beneficial already after the first infection episode, such as a first *Clostridium difficile* infection or another infection episode, in order to prevent recurrence of infection or occurrence of a different infection.

Thus, in one embodiment it is provided a pharmaceutical composition for use as disclosed herein, wherein said administration begins at least 1 day, such as at least 2 days, such as 3 days or more, after the completion of the antibiotic treatment. In some embodiments, said administration begins within 1-5 days, such as 2-5 days, such as 2-4 days, such as 2-3 days or 1-4 days, such as 1-3 days, such as 1-2 days after the completion of the antibiotic treatment. In one embodiment, it is provided a pharmaceutical composition for use as disclosed herein, wherein a first administration event occurs at least 1 day, such as at least 2 days, such as 3 days or more, after the completion of the antibiotic treatment. In some embodiments, said administration occurs 1-5 days, such as 2-5 days, such as 2-4 days, such as 2-3 days or 1-4 days, such as 1-3 days, such as 1-2 days after the completion of the antibiotic treatment. For example, said first administration event occurs within 1-5 days, such as 2-5 days, such as 2-4 days, such as 2-3 days or 1-4 days, such as 1-3 days, such as 1-2 days after the completion of the metronidazole and/or vancomycin and/or fidaxomicin treatment.

As explained in context of the first aspect, wherein there is a risk for developing a first *Clostridium difficile* infection (for example when a patient undergoes antibiotic treatment), it may be beneficial to prevent such development. Thus, in one embodiment it is provided a pharmaceutical composition for use as disclosed herein, wherein said administration begins at least 1 day, such as at least 2 days, such as 3 days or more, after the completion of the antibiotic treatment, which antibiotic treatment targets at least one different infectious agent than *Clostridium difficile*. In some embodiments, said administration begins within 1-5 days, such as 2-5 days, such as 2-4 days, such as 2-3 days or 1-4 days, such as 1-3 days, such as 1-2 days after the completion of an antibiotic treatment, which antibiotic treatment targets at least one different infectious agent than *Clostridium difficile*. For example, said antibiotic treatment may target an infectious agent selected from *Salmonella*, EHEC, ETEC, *Klebsiella* and *Shigella* or another bacterial strain. The skilled person appreciates that the above examples are non-limiting. In one embodiment, it is provided a pharmaceutical composition for use as disclosed herein, wherein a first administration event occurs at least 1 day, such as at least 2 days, such as 3 days or more, after the completion of the antibiotic treatment, which antibiotic treatment targets at least one different infectious agent than *Clostridium difficile*. In some embodiments, said administration occurs within 1-5 days, such as 2-5 days, such as 2-4 days, such as 2-3 days or 1-4 days, such as 1-3 days, such as 1-2 days after the completion of the antibiotic treatment, which antibiotic treatment targets at least one different infectious agent than *Clostridium difficile*. In one embodiment, said antibiotic treatment is a broad spectrum antibiotic treatment.

It will be appreciated that it may be beneficial to administer said pharmaceutical composition as disclosed herein to a subject who is at risk of developing an infection caused by any of the above mentioned pathogens as discussed in the context of the first aspect as disclosed herein.

As discussed above, it will be appreciated that non-invasive administration may be generally preferable. Thus, in one particular embodiment, said pharmaceutical composition is formulated for oral administration, such as oral self-administration, such as out-patient oral self-administration. Said pharmaceutical composition may be formulated as a capsule, a pill, or a tablet for oral administration. For example, said composition may be formulated as an enteric resistant capsule, such as a capsule with an enteric coating. An enteric coating is a polymer barrier which may be applied on oral medication to prevent its dissolution or disintegration in the gastric environment. Thus, in one embodiment there is provided a pharmaceutical composition as disclosed herein, which composition is formulated as a capsule, a pill or a tablet, such as a capsule or tablet, such as an enteric resistant tablet or capsule.

As used herein, the term "colony forming units" or "CFU" refers to aerobic viable counts, anaerobic viable counts or both aerobic and anaerobic viable counts.

In one embodiment, there is provided a pharmaceutical composition as disclosed herein, wherein said therapeutically effective amount is at least $1\times10^7$ CFU, such as at least $1\times10^8$ CFU, such as at least $1\times10^9$ CFU, such as at least $1\times10^{10}$ CFU of said live microorganisms per administration event.

It will be appreciated that is convenient to be able to store the pharmaceutical composition in a ready to administer form at least for the administration period. Thus in one embodiment, there is provided a pharmaceutical composition as disclosed herein, which is stable at 4-10° C., such as 4-8° C., or at −20° C. or at ≤−70° C. for a period of at least 10 days, such as at least 20 days, such as at least 30 days, such as at least 45 days, such as at least 60 days.

In one embodiment, said pharmaceutical composition comprises at least $1\times10^7$ CFU, such as at least $1\times10^8$ CFU, such as at least $1\times10^9$ CFU of said live microorganisms after at least 10 days, such as at least 20 days, such as at least 30 days, such as at least 45 days, such as at least 60 days, of storage at 4-10° C., such as at 4-8° C., or at −20° C. or at ≤−70°.

It will be appreciated that the embodiments discussed above in relation to the first aspect of the present disclosure are equally relevant for this present aspect of the disclosure.

Thus, in one embodiment there is provided a pharmaceutical composition for use as disclosed herein, wherein the administration of said pharmaceutical composition comprises 1-10 administration events per day, such as 1-9 administration events per day, such as 1-8 administration events per day, such as 1-6 administration events per day, such as 2-6 administration events per day, such as 3-6 administration events per day or 2-4 times per day, such as 2, 3 or 4 administration events per day. In one embodiment, said administration is 1, 2, 3, 4, 5, 6, 7, 8, 9 or 10 administration events per day. In one embodiment, said administration is administration at 1, 2 or 3 separate occasions per day, such as 1 or 2 separate occasions per day. In one embodiment, said occasions are separated by at least 4 hours, such as at least 6 hours, such as at least 8 hours or at least 12 hours. In one embodiment, 1, 2, 3, 4 or 5, such as 1, 2, 3, or 4 doses are administered at each said occasion. In one embodiment, 1, 2 or 3 doses are administered at each occasion, such as 1 or 2 doses. In one embodiment, said administration is continued for a period of at least 5 days, such as for 5-30 days, such as 5-14 days, such as 5-10 day. In one embodiment, said administration is continued for 5-7 days, such as for 5 or 7 days, for example 5, 6 or 7 days. In one embodiment, said administration is continued for 10 days. In one embodiment, said administration is continued for any of 5, 6, 7, 8, 9 or 10 days. In one embodiment, said administration is for 1-4 days, such as 1, 2, 3, or 4 days.

It is envisioned that the pharmaceutical composition as disclosed herein may further comprise an additional therapeutic agent, for example an agent which provides beneficial condition for recolonization of the gastrointestinal tract or an immunosuppressive agent. Thus, in one embodiment, there is provided a pharmaceutical composition as disclosed herein further comprising an additional therapeutic agent.

In the third aspect of the present disclosure, there is provided a related method for the prevention and/or treatment of microbial dysbiosis in the gastrointestinal tract, comprising orally administering to a subject in need thereof a therapeutically effective amount of an autologous fecal sample as disclosed herein or a pharmaceutical composition as disclosed herein, wherein said administration comprises 1-10 administration events per day for 1-30 days.

In one embodiment, said method comprises autologous reconstitution of normal microbiota of the gastrointestinal tract, such as the normal microbiota downstream of the duodenum. In particular, said autologous reconstitution comprises repopulation of the gastrointestinal tract with at least one desired species of microorganism, for example bacteria. In particular, said reconstitution may comprise repopulation of the gastrointestinal tract with said at least one species of microorganism, for example bacteria. In one embodiment, said repopulation is repopulation with at least 50% such as with at least 60%, such as at least with 70%, such as at least with 80%, such at least with 90% of the desired species of microorganism, such as desired bacterial species. In one embodiment, said repopulation is repopulation with at least 25% such as with at least 50%, such as at least with 75%, such as at least with 80%, such at least with 90% of the phyla and/or genera discussed previously.

As discussed in connection with previous aspect as disclosed herein, said microbial dysbiosis may be a microbial dysbiosis caused by medical treatment, such as antibiotic treatment or a microbial dysbiosis associated with a disease. Thus, in one embodiment, there is provided a method as disclosed herein, wherein said microbial dysbiosis caused by medical treatment. Said medical treatment may be antibiotic treatment or by other medical treatment, such as a medical treatment is selected from the group consisting of immunosuppressive treatment; cytostatic treatment; radiation treatment; surgical treatment; and treatment with biguanides, such as metformin. Said treatment may be an earlier treatment or a concomitant treatment as discussed above. In one embodiment, said microbial dysbiosis is associated with a chronic disease affecting the gastrointestinal tract, such as a chronic disease selected from the group consisting of irritable bowel syndrome, Crohn's disease, ulcerative colitis, collagenous colitis and diverticulitis. In one embodiment, said microbial dysbiosis is associated with an infectious disease affecting the gastrointestinal tract selected from the group consisting of disease caused by a bacterial infection, such as an infection by *Clostridium, Salmonella*, EHEC, ETEC, *Klebsiella* or *Shigella*; a viral infection, such as an infection by calicivirus or ROTA-virus; and a parasitic infection, such as an infection by *Crytosporidium* or *Giardia*. In one embodiment, said microbial dysbiosis is associated with a bacterial infection selected from the group consisting of infections by *Clostridium, Salmonella*, EHEC, ETEC, *Klebsiella* and *Shigella*.

In particular, there is provided a method as disclosed herein, said microbial dysbiosis is associated with a *Clostridium difficile* infection, such as an ongoing *Clostridium difficile* infection or an earlier *Clostridium difficile* infection. In one embodiment, said prevention and/or treatment is carried out post at least one *Clostridium difficile* infection. For example, said prevention is the prevention of occurrence or recurrence of a *Clostridium difficile* infection. Furthermore, said prevention may be the prevention of *Clostridium difficile* translocation across the intestinal membrane. In one embodiment, there is provided a method as disclosed herein, wherein said *Clostridium difficile* infection is a first *Clostridium difficile* infection.

In particular as discussed in detail in the context of the first and second aspect, it is envisioned that said method may be beneficial for a patient who undergoes and completes an antibiotic treatment, such as an antibiotic treatment targeting *Clostridium difficile* infection or another infection, in order to achieve reconstitution of the microbiota in the gastrointestinal tract and thus prevent the recurrence or reduce the risk of recurrence of said infection or the occurrence of a different infection. It is envisioned that the method is beneficial already after the first infection episode, such as a first *Clostridium difficile* infection or another infection episode, in order to prevent recurrence of infection or occurrence of a different infection.

Thus, in one embodiment it is provided a method for prevention and/or treatment as disclosed herein, wherein said administration begins at least 1 day, such as at least 2 days, such as 3 days or more, after the completion of the antibiotic treatment. In some embodiments of said method, said administration begins within 1-5 days, such as 2-5 days, such as 2-4 days, such as 2-3 days or 1-4 days, such as 1-3 days, such as 1-2 days after the completion of the antibiotic treatment.

In one embodiment, there is provided a method for prevention and/or treatment as disclosed herein, wherein said administration begins within 1-5 days, such as 2-5 days, such as 2-4 days, such as 2-3 days or 1-4 days, such as 1-3 days, such as 1-2 days, after the completion of the antibiotic treatment. In one embodiment of said method, a first administration event occurs within 1-5 days, such as 2-5 days, such as 2-4 days, such as 2-3 days or 1-4 days, such as 1-3 days, such as 1-2 days, after the completion of the antibiotic treatment. For example, said first administration event occurs within 1-5 days, such as 2-5 days, such as 2-4 days, such as 2-3 days or 1-4 days, such as 1-3 days, such as 1-2 days after the completion of the metronidazole and/or vancomycin and/or fidaxomicin treatment.

As explained in context of the first and second aspect, wherein there is a risk for developing a first *Clostridium difficile* infection (for example when a patient undergoes antibiotic treatment), it may be beneficial to prevent such development. Thus, in an embodiment of the method for prevention and/or treatment as disclosed herein, wherein said administration begins at least 1 day, such as at least 2 days, such as 3 days or more, after the completion of the antibiotic treatment, which antibiotic treatment targets at least one different infectious agent than *Clostridium difficile*. In some embodiments, said administration begins within 1-5 days, such as 2-5 days, such as 2-4 days, such as 2-3 days or 1-4 days, such as 1-3 days, such as 1-2 days after the completion of an antibiotic treatment, which antibiotic treatment targets at least one different infectious agent than *Clostridium difficile*. For example, said antibiotic treatment may target an infectious agent selected from *Salmonella*, EHEC, ETEC, *Klebsiella* and *Shigella* or another bacterial strain. The skilled person appreciates that the above examples are non-limiting. In one embodiment, it is provided a method as disclosed herein, wherein a first administration event occurs at least 1 day, such as at least 2 days, such as 3 days or more, after the completion of the antibiotic treatment, which antibiotic treatment targets at least one different infectious agent than *Clostridium difficile*. In some embodiments, said administration occurs within 1-5 days, such as 2-5 days, such as 2-4 days, such as 2-3 days or 1-4 days, such as 1-3 days, such as 1-2 days after the completion of the antibiotic treatment, which antibiotic treatment targets at least one different infectious agent than *Clostridium difficile*. In one embodiment, said antibiotic treatment is a broad spectrum antibiotic treatment.

It will be appreciated that it may be beneficial to administer said pharmaceutical composition as disclosed herein to a subject who is at risk of developing an infection caused by any of the above mentioned pathogens as discussed in connection with the first and second aspects.

As discussed above, the route of administration is important for subject compliance as well as for how the subject experiences a treatment. Thus, in one embodiment of said method, the oral administration is oral self-administration, such as out-patient oral self-administration.

In one embodiment of said method, said administration comprises 1-10 administration events per day, such as 1-9 administration events per day, such as 1-8 administration events per day, such as 1-6 administration events per day, such as 2-6 administration events per day, such as 3-6 administration events per day or 2-4 times per day, such as 2, 3 or 4 administration events per day. In one embodiment, said administration is 1, 2, 3, 4, 5, 6, 7, 8, 9 or 10 administration events per day. In one embodiment, said administration is administration at 1, 2 or 3 separate occasions per day. In one embodiment, said occasions are separated by at least 4 hours, such as at least 6 hours, such as at least 8 hours or at least 12 hours. In one embodiment, 1, 2, 3, 4 or 5, such as 1, 2, 3, or 4, doses are administered at each said occasion. In one embodiment, 1, 2 or 3 doses, such as 1 or 2 doses, are administered at each occasion, such as 1 or 2 doses. In one embodiment, said administration is continued for a period of at least 5 days, such as for 5-30 days, such as 5-14 days, such as 5-10 day. In one embodiment, said administration is continued for 5-7 days, such as for 5 or 7 days, for example for 5, 6 or 7 days. In one embodiment, said administration is continued for 10 days. In one embodiment, said administration is continued for any of 5, 6, 7, 8, 9 or 10 days. In one embodiment, said administration is for 1-4 days, such as 1, 2, 3, or 4 days.

In one particular embodiment, said method may further comprise administration of an additional therapeutic agent. For example, an additional therapeutic agent may be an agent which provides beneficial condition for recolonization of the gastrointestinal tract. Alternatively, said agent may be an immunosuppressive agent. Said agent may be administered concomitantly or sequentially in respect to the administration of said autologous feces sample or said pharmaceutical composition. It is also envisioned that said agent is administered prior to or simultaneous with administration of said autologous feces sample or said pharmaceutical composition in order to provide a beneficial environment for the recolonization of the gastrointestinal tract.

It is furthermore contemplated that the autologous fecal sample or pharmaceutical composition as defined herein and an additional therapeutic agent are combined into a combination kit. For example, a combination kit could comprise a dosage form of the autologous feces sample or pharmaceutical composition as described herein and a dosage form of additional therapeutic agent. Additionally, said kit may comprise printed matter with information and/or a suitable box container for storage of said agents. The kit is envisioned to provide all components necessary for the administration of the autologous feces sample or pharmaceutical composition and the additional therapeutic agent in a safe and convenient manner.

Thus, in a fifth aspect as disclosed herein, there is provided a kit comprising i) an autologous fecal sample as defined herein or a pharmaceutical composition as defined herein and ii) an additional therapeutic agent. It may also be beneficial to provide an agent prior to or simultaneously with administration of said autologous feces sample or said pharmaceutical composition in order to provide a beneficial environment for the recolonization of the gastrointestinal tract. In one embodiment of said kit, the additional therapeutic agent is an immunosuppressive agent.

In one embodiment of said kit, the additional therapeutic agent is formulated for oral, subcutaneous, intramuscular or intravenous administration, such as oral or intravenous administration, in particular oral administration.

In a related aspect, there is provided a kit comprising i) an autologous fecal sample as defined herein or a pharmaceutical composition as defined herein and ii) an additional agent effective to promote bacterial repopulation.

In one particular embodiment of either kit, there is provided a kit wherein said autologous fecal sample and said additional agent are formulated for concomitant or simultaneous administration. In this context, concomitant administration is considered administration of at least two agents within less than 48 hours of each other. Thus, in one embodiment a kit is provided, wherein said sample and agent are formulated for concomitant administration within less than 48 hours of each other, such as within less than 24 hours, such as within less than 12 hours, such as within less than 6 hours.

It is also envisioned that it may be useful for the subject to swallow a test oral dosage form, such as a capsule, prior to beginning administration of the autologous fecal sample or pharmaceutical composition as defined herein in order to ensure that no difficulties are experienced during swallowing. Said test swallowing may be performed one time at the beginning of the administration period or at the beginning of every administration occasion. Such test oral dosage form, such as capsule, is expected to be of the same size and outer texture as the oral dosage form comprising said autologous fecal sample or pharmaceutical composition. However, the test oral dosage form does not comprise any therapeutically active agent. The test oral dosage form may comprise placebo and/or pharmaceutically acceptable carriers and/or excipients.

Thus, in yet another aspect of the present disclosure, there is provided a kit comprising a) at least one oral dosage form comprising an autologous fecal sample as defined herein or a pharmaceutical composition as defined herein and b) at least one corresponding oral dosage form which does not comprise any therapeutically active agent. In one embodiment, said oral dosage forms in a) and b) are a capsules, such as enteric capsules.

In an additional aspect of the present disclosure, there is provided the use of an autologous fecal sample as defined herein for the manufacture of a medicament for the prevention and/or treatment of microbial dysbiosis in the gastrointestinal tract of a subject in need thereof.

While the invention has been described with reference to various exemplary aspects and embodiments, it will be understood by those skilled in the art that various changes may be made and equivalents may be substituted for elements thereof without departing from the scope of the invention. Therefore, it is intended that the invention not be limited to any particular embodiment contemplated, but that the invention will include all embodiments falling within the scope of the appended claims.

EXAMPLES

The present examples describe a clinical study that aims to assess the safety and tolerability of capsules containing autologous microbiota compared to placebo in healthy volunteers after antibiotic exposure. The time to recovery of intestinal microbiota is determined using a next generation sequencing platform. The present inventors have established a method whereby subjects can leave a stool samples for example prior to planned treatment, such as antibiotic exposure; prior to planned pathogen exposure; and/or during a remission period of a chronic disease. The samples can later be used for therapeutic treatment and/or prophylactic treatment in order to reconstitute the intestinal microbiota.

Example 1

Study Design and Study Population

In Example 1 the design of the clinical study in described as well as the criteria relating to the study population.

Study Design:

A double blind placebo controlled phase 1 clinical trial is conducted at Danderyds Hospital, Danderyd, Sweden.

Twenty four volunteers are included in the study. Following informed consent participants (also termed subjects) are requested to donate feces. Participants are randomized into treatment group A, B or C. Treatment consists of clindamycin for seven days for all participants independent of treatment group. The clindamycin treatment is followed by intake of identical capsules containing placebo or feces solution dependent on the treatment group A or B for a period of 5 days. Thus, participants in group A are treated with clindamycin followed by administration of capsules with feces solution while participants in group B (control group) are treated with clindamycin followed by administration of placebo capsules. The administered fecal sample in the form of feces solution or diluted feces solution is autologous to the participant. Participants' general health and gastrointestinal symptoms is monitored using questionnaires. Stool samples for sequencing of the microbiota according to Example 4 are collected as described below.

Study Population:

The study population is healthy non-pregnant volunteers aged 18-40 years and includes 24 subjects. The following inclusion and exclusion criteria apply:

Inclusion Criteria:

Written informed consent after meeting with a study physician and the ability to swallow a placebo capsule.

Exclusion Criteria:

History of or ongoing disturbed bowel condition, delayed gastric emptying syndrome, recurrent aspirations, swallowing dysfunction, inability to swallow large capsules, antibiotic treatment during the previous 3 months, regular intake of any medication, body mass index<18.5 and >30, any other significant medical history (except resolved traumatic injury). Identification of *C. difficile* in stool sample prior to study start.

Prior and Concomitant Medications:

Medication history (prior medications) was collected prior to study start, including prescription medications, over-the-counter (OTC) medications, and herbal products. Any changes in concomitant medications changes reported by the subject were be recorded.

Results:

24 subjects are enrolled in the study and are divided into study group A and control group B as described above.

Study Subject Characteristics:

Subject demographics are summarized in Table 1. Subject age ranges are from 21-40 years, with a mean of 32 years. There are 10 females and 14 males.

TABLE 1

Summary of subject demographics.

| Age range | Age mean | Gender | Number |
|---|---|---|---|
| 21-40 yrs. | 32 yrs. | Female | 10 |
| | | Male | 14 |

Example 2

Study Procedures

In Example 2 the preparation of the autologous fecal samples as well as the conduct of the clinical study are described.

Preparation and Storage of Inoculate:

Following inclusion volunteers were requested to leave a fecal sample. The fecal sample was left at the hospital unit. The fecal sample was sampled for microbiological testing and the remaining material is transported to facility for preparation as described below. The fecal samples are homogenized, filtered and glycerol is added before freezing. Fecal sample are centrifuged twice at 200-400 g for 10-30 minutes to separate more course material from feces. If needed sample is first diluted in saline. Then the feces solution/slurry is centrifuged at 4000-6000 g for 10-30 minutes. The pellet is suspended in glycerol and then frozen in plastic tube at −80° C. Freezing is done within 12 h after collection and samples remain frozen for 8-30 days. The fecal samples are thawed and a formulation is prepared. Each frozen sample was thawed and mixed with Tween 80 and vegetable oil and homogenized. Thus, the obtained formulation is a mixture of autologous feces, saline, glycerol, vegetable oil and Tween 80 according to Table 2.

TABLE 2

Formulation prepared according to the present disclosure.

|  | Component | Reference to standards | Function |
|---|---|---|---|
| Autologous fecal sample | Autologous feces | NA | Active ingredient |
|  | Physiological Saline Solution | Ph. Eur | Diluent |
|  | Glycerol | Ph. Eur. | Cryoprotectant |
|  | Tween 80 | Ph. Eur. | Homogenizing agent |
|  | Vegetable oil | Ph. Eur. | Diluent |
| Placebo control | Vegetable oil | Ph. Eur. | Diluent |

Placebo controls consist of vegetable oil. This formulation is then filled in enteric resistant capsules comprising at least $1 \times 10^7$ CFU each or at least $1 \times 10^8$ CFU each.

The final feces mixture or placebo control is filled into acid resistant capsules size 0. The capsule was then put into a second, slightly larger acid resistant capsule size 00. Capsules are made of hydroxyproyl methylcellulose. The volume of capsules size 0 capsule is 0.60 ml and the size of the final capsule, e.g the size of the 00 capsules is 23.4×8.56 mm. The capsules are packaged into a plastic jar and labelled with patient number and distributed to the clinic. Capsules are stored at −20° C. The product filled into acid resistant capsules is expected to be stable for at least 30 days at −20° C.

Randomization of Study Subjects:

Patients who fulfill all the inclusion criteria and none of the exclusion criteria are randomized into two arms:

Group A: Clindamycin+Capsules with autologous feces solution

Group B: Clindamycin+Placebo Capsules (control)

Identical paper slips specifying group A or B (12 of each) will be put into an envelope. Participants randomly select one slip.

Treatment code envelopes are provided for each randomized subject. The treatment code is not broken until all assessments had been performed, all data had been entered into the database and the database has been locked. Only in the event of a serious adverse effect, the blind is allowed to be broken for that specific subject.

Treatment:

Participants arrive to the hospital unit the day prior to treatment start to collect clindamycin and for a final briefing. All participants were requested to take 300 mg clindamycin capsules morning, lunch and evening for seven days. This is followed by a two-day washout period. On day two of the washout period participants return to the hospital unit to collect their respective study capsules that are to be stored in a freezer at home. Participants are then requested to take two study capsules twice daily for 5 days.

An SMS text message is sent twice daily to remind volunteers to take the clindamycin and study capsules. Subjects and investigators are blinded as to the content of the capsules. The code is held by the manufacturers of the capsules that are not involved in the clinical part of the study.

TABLE 3

Outline of clinical study and sampling protocol.

| | | Days | | | | | | |
|---|---|---|---|---|---|---|---|---|
| | 1 | 1-7 | 8-10 | 10-15 | 16 | 28 | 2 months | 6 months |
| | | | Phase of study | | | | | |
| | Inclusion | Start | Antibiotic | Washout | Treatment | | Follow up | |
| CRF A | + | | | | | | | |
| C. diff. screening | + | | | | | | | |
| Fecal sample* | + | + | | + | | + | + | + | + |
| CRF B | | + | + | + | + | + | + | + | + |
| Hospital visit | + | + | | + | | + | | | |

*Prior to study start a fecal sample for autologous transplant will be donated.

Stool samples for sequencing are taken at baseline and on days 10, 16 (+3 days if necessary), 28 and at 2 and 6 months.

Monitoring and Follow Up:

Upon inclusion clinical record forms will be completed.

Stool habits and characteristics are monitored daily from treatment start using a structured questionnaire. The questionnaire is used to record stool frequency and consistency, general and gastrointestinal well-being via a standardized health score (according to the Bristol stool chart, Table 3), rating of gastrointestinal symptoms and medication use. Overall and gastrointestinal-specific health scores are reported on a scale of 1 to 10, with 1 being the lowest and 10 being "best possible health for you".

TABLE 4

Bristol stool chart.
Bristol stool chart

| | |
|---|---|
| Type 1 | Separate hard lumps, like nuts (hard to pass). |
| Type 2 | Sausage-shape but lumpy |
| Type 3 | Like a sausage but with cracks on its surface |
| Type 4 | Like a sausage or snake, smooth and soft |
| Type 5 | Soft blobs with clear-cut edges, a mushy stool |
| Type 6 | Fluffy pieces with ragged edges, a mushy stool |
| Type 7 | Watery, no solid pieces. Entirely liquid |

Adverse Events:

Possible adverse events (AE) are monitored elicited using a modification of the Common Terminology Criteria for Adverse Events version 3.0. as disclosed in Youngster et al Jama 2014; 312(17): 1772-8 and Trotti A et al Semin Radiat Oncol 2003; 13(3): 176-81. Fever, gastrointestinal symptoms (including diarrhea, nausea/bloating, abdominal pain, vomiting), fatigue/malaise/headache and rash are principle symptoms evaluated.

In the present study, an AE in this study was defined as any untoward medical occurrence in a subject who has received investigational medicinal product (IMP). The occurrence did not necessarily need to have a causal relationship with the IMP. An AE could therefore be any unfavorable and unintended sign (including an abnormal laboratory finding), symptom, or disease temporally associated with the administration of IMP, whether or not causally related. If any serious AE (SAE) would occur during the study, they are to be reported to the investigator and handled according to established procedures. Subjects are requested to self-estimate potential adverse effects according to the following Table 5.

Results:

The safety and efficacy outcomes, in terms of clinical record of stool habits and characteristics, are assessed.

Safety:

It is expected that only mild AE are observed in subjects during the treatment period. It is expected that a lower frequency of AE and/or milder AE are observed compared AE reported in Youngster et al 2016. No SEA are expected.

TABLE 5

Adverse side effects.

| | | Mild- 1 | Moderate -2 | Serious -3 | Potentially life threatening |
|---|---|---|---|---|---|
| Severity degree - general | | | | | |
| | | Symptoms have no or minimal effect on daily life | Symptoms have more than minimal effect on daily life | Symptoms prevent aspects of daily life | Symptoms prevent basal care or lead to medical or surgical intervention to prevent permanent injury |
| Symptom specific severity degree | | | | | |
| | Fever | 38-39 | >39-40 | >40 | >40 for >24 h |
| | Diarrhea | Transient episodes or an increase of ≤3 stools per day | Persistent diarrhea or an increase by 4-6 stools per day | Bloody diarrhea or an increase of ≥7 stools per day or need of IV fluids | Life threatening, e.g. hypotensive chock |
| | Nausea | Transient <24 h or intermittent nausea | Persistent nausea causing decrease intake per os for 24-48 h | Persistent nausea causing minimal intake per os for >48 h or requires IV fluids | Life threatening |
| | Vomiting | Transient or intermittent vomiting with minimal effect on intake per os | Frequent vomiting with light dehydration | Persistent vomiting with ortostatic hypotension or need of IV fluids | Life threatening |
| | Fatigue/feeling of sickness | Symptoms have no or minimal effect on daily life | Symptoms have more than minimal effect on daily life | Symptoms prevent aspects of daily life | Debilitation fatigue leading to inability to maintain basal care |

TABLE 5-continued

Adverse side effects.

| | Mild- 1 | Moderate -2 | Serious -3 | Potentially life threatening |
|---|---|---|---|---|
| Headache | Symptoms have no or minimal effect on daily life | Symptoms have more than minimal effect on daily life | Symptoms prevent aspects of daily life | Headache leading to inability to maintain basal care or inhibits neurological or cognitive functions significantly. |

Efficacy:

The efficacy of the autologous fecal sample treatment is evaluated based on the self-estimation questionnaire monitoring the stool frequency and consistency, general and gastrointestinal well-being via a standardized health score (according to the Bristol stool chart, Table 3) and gastrointestinal symptoms. Overall and gastrointestinal-specific health scores are reported on a scale of 1 to 10, with 1 being the lowest and 10 being "best possible health for you".

It is expected that after treatment the subjects will report an improvement of stool frequency and consistency. Additionally, the general and gastrointestinal well-being via a standardized health score is expected to be improved in the subject population.

After unblinding the study groups, the clinical outcomes will be compared between group A and group B and statistical analysis will be performed. It is expected that the resolution of clinical symptoms in group A is achieved in a significantly shorter period of time than in group B, including the time until improvement of stool frequency and consistency, and/or improvement of general and gastrointestinal well-being. Also, group A is expected to achieve reconstitution/normalization of the gastrointestinal microbiome in a significantly shorter period of time compared to the control group B.

Example 3

Laboratory Procedures

In Example 3 the laboratory procedures involved in fecal sample (also referred to as stool sample) handling and storage are described.

Stool Sampling for Capsule Preparation:

The samples and capsules were prepared as described in Example 2. A same day stool sample (minimum volume approximately 2 table spoons full) stored in a dedicated container is delivered to the hospital unit on the day that antibiotic treatment starts.

Stool Sampling for Sequencing:

A dedicated container is given for stool sampling. Samples are sent to for analysis. Samples will be analyzed as described in Example 4.

Biobank:

Stool samples and blood samples are stored as part of the Karolinska Institutet biobank.

Example 4

Study of the Intestinal Microbiota

In this Example, the time to reconstitution of the intestinal microbiota is be assessed using a Clinical Genomics platform. The Clinical Genomics platform is a high-scale throughput next generation sequencing based platform for the analysis of intestinal microbiota. The bacterial composition is determined by analysis of bacterial 16S rRNA gene that contains stable regions, suitable for primers and variable regions, suitable for species identification. This platform is used to determine the rate at which the composition of intestinal microbiota is normalized after treatment with the orally administered autologous fecal sample as disclosed herein.

Study of the Intestinal Microbiota:

In order to study the intestinal microbiota a massive parallel sequencing approach is performed. The subject takes a stool sample (approximate one table spoon in a dedicated container as mentioned above) immediately after defecation and introduce it into a transport medium for subsequent microbiota analyses in a dedicated container. Samples are sent by ordinary mail (using standard shipping procedures) to the laboratory and frozen upon arrival at −80° C.

Sequencing libraries for microbiota profiling are prepared by amplifying the V3-V4 region of the 16S rRNA gene. After the initial amplification a second PCR is performed to attach Illumina adapters as well as barcodes that allows for multiplexing. Samples are sequenced using the Illumina MiSeq, whereafter primer sequences are trimmed away and the paired-end reads produced by the sequencing instrument are merged using SeqPrep version 1.1 (https://github.com/jstjohn/SeqPrep) with default parameters and thereafter processed with the QIIME 1.8.0 pipeline (Quantitative Insight Into Microbial Ecology). Using this pipeline, sequences are clustered at 97% identity against the Greengenes reference database (Caporaso J G et al., Nat Methods 2010; 7(5): 335-6).

Results:

It is expected that before initiation of treatment of with autologous fecal samples, but after completion of the clindamycin treatment, the fecal microbiotic profile of subjects in both group A and group B exhibit lower microbial diversity as compared to fecal samples obtained before clindamycin treatment (study day 1 or earlier). After the clindamycin treatment, fecal samples obtained from subjects in group A and B are expected to exhibit characteristics of dysbiosis. Clindamycin treatment is expected to lead to a decrease of gram-positive aerobic and anaerobic bacteria and to a shift in microbial population at genus level, including reduction of *Coprococcus, Roseburia, Lacchospira, Dorea, Ruminococcus* and Lachonospiraceae. Also, it is expected that the clindamycin induced dysbiosis will exhibit a decrease in lactobacilli, entrerococci and bifidobacteria.

Comparison of microbiota profile in fecal samples obtained at time points day 16, day 28, 2 months and 6 months of the study is expected to show that reconstitution of microbiota (as measured in fecal samples) occurs faster in subjects from group A compared to subjects from group B. Furthermore, it is expected that the microbiota profile in fecal samples obtained from subjects in group A will exhibit a high degree of similarity with the initial microbiota profiles obtained from samples before clindamycin treatment. This profile is expected to be representative of the capsulated autologous fecal samples administered.

Furthermore, it possible that the microbiota profile in fecal samples obtained from subjects in group B will exhibit a lower degree of similarity with the initial microbiota profiles obtained from samples before clindamycin treatment or that said microbiota profile will be divergent from said initial microbiota profile.

After unblinding the study groups, the distribution of phyla/genus/species will be compared between group A and group B and statistical analysis will be performed. Subject administered capsules with autologous fecal sample (group A) are expected to exhibit a normalization or reconstitution of the intestinal microbiota earlier than subjects administering capsules with placebo (group B).

Example 5

Example 5 discloses further details regarding expected outcomes of the study and statistical analysis employed.

Outcomes:

Primary end points are safety and tolerability, as defined by any microbiota related adverse events at grade 2 or above. Secondary end points include time to reconstituted or normalized intestinal microbiota and determining non-severe adverse events.

Statistical Analysis:

Power Calculation:

No power calculation is performed for this phase 1 safety and tolerability study. Twelve subjects in each arm are considered sufficient to detect major adverse events whilst avoiding unnecessary exposures.

Data Analysis:

Final analysis includes a description of included participants, proportions of adverse events and any serious adverse events, the proportion of participants withdrawn or lost to follow up. Categorical variables are compared between subject groups using the $\chi^2$ test or Fisher exact test and continuous variables using quantile regression.

For microbiota Shannon indexes for alpha diversity are calculated in all samples and tested for significance with Wilcoxon rank-sum test. Also, beta diversity is calculated. Using the QIIME pipeline, unweighted UniFrac distances are then produced and used for investigation of beta diversity through plotting PCA coordinates. It is expected that reconstitution of microbiota and normalization of the diversity thereof occurs faster in subjects from group A compared to subjects from group B.

Example 6

The present example describes a stability study of the bacterial viable counts in feces from the time of collection and at all process steps until an anticipated use of the feces.

Materials and Method:

Collected fecal samples are diluted with a cryoprotectant and immediately frozen to $\leq-70°$ C. and stored for various length of time, thawed and formulated with the addition of a surfactant and vegetable oil. The formulated fecal samples are filled into capsules and stored at various temperature conditions for various times.

Samples from each step of the handling of the fecal material are taken for bacterial viable counts (aerobic and anaerobic) by standard bacteriological techniques (10-fold dilution) on nonselective agar mediums.

Results:

The results from the stability studies were as follows: Aerobic VC (viable counts) directly after collection of feces: $10^{10}$/ml; after 1 day in the freezer at $\leq-70°$ C.: $10^{10}$/ml; and after 3 months in the freezer at $\leq-70°$ C.: $10^{10}$/ml. After formulation and before encapsulation the aerobic VC is expected to be $5\times10^9$/ml.

After storage for 6 weeks the aerobic VC was as follows: $5\times10^8$/ml after storage at 4-8° C.; and $10^9$/ml after storage at $-20°$ C. and at $\leq-70°$ C. The dilution of feces has been taken into account for the presented counts.

Anaerobic viable counts are in general 10 times higher.

The present experiment shows that stability of the fecal sample is maintained over a period of at least 6 weeks based on viable counts (summarized in Table 6). Thus, the fecal samples as used according to the present disclosure are stable in terms of viability of their bacterial composition.

TABLE 6

Results from 6 week stability study.

|  | At collection | 6 weeks 4-8° C. | 6 weeks −20° C. | 6 weeks ≤−70° C. |
|---|---|---|---|---|
| Aerobic VC | $1 \times 10^{10}$/ml | $5 \times 10^8$/ml | $1 \times 10^9$/ml | $1 \times 10^9$/ml |
| Anaerobic VC | $1 \times 10^{11}$/ml | $5 \times 10^9$/ml | $1 \times 10^{10}$/ml | $1 \times 10^{10}$/ml |

Additionally, the stability of fecal samples is studied after at storage period of over 1 year at $-20°$ C. or at $\leq-70°$ C. The sample is obtained fresh from a donor alternatively from a fecal sample culture obtained from ACHIM Biotherapeutics AB, Stockholm, Sweden. As above, VC analysis is performed for aerobic and anaerobic bacteria.

Example 7

The present example describes a case study of administration of capsules containing autologous microbiota compared in a CDI patient after antibiotic exposure (metronidazole and/or vancomycin and/or fidaxomicin with or without alternative antibiotics). Said CDI patient suffered from recurrent, refractory or severe CDI. The case study demonstrates the rate and efficacy of CDI cure after administration of oral capsules containing autologous microbiota as well as any adverse effect experienced by the patient.

Results: It is expected that the CDI patient will recover dramatically faster from the disease after administration of the capsule and that additional treatment i.e. oral vancomycin or metronidazole treatment to cure the infection will not be indicated. Consequently, the frequency of diarrhea will decrease and the overall well-being of the patient will improve faster than expected. The gut microbiota profile (fecal samples) will show higher diversity index and a normalization of the beta diversity (see above).

Example 8

The present Example describes a clinical study that aims to assess the safety, tolerability and efficacy of autologous microbiota compared to patients not receiving any treatment in patients after exposure to broad spectrum antibiotic treatment.

In this study, patients suffering from severe burns are treated with broad spectrum antibiotics, causing gastrointestinal dysbiosis and increasing the risk for developing CU and selection of resistant bacterial species in the gut microbiome.

Before the initiation of antibiotic treatment fecal samples are obtained from the patients and the samples are prepared for administration either by colonoscopy or by the oral route. Samples are prepared for oral administration essentially as described in Examples 2 and 3.

1-5 days after completion of antibiotic treatment the patient is administered the autologous fecal sample. In the case of oral administration capsules comprising autologous fecal samples are administered for a period of 1-30 days, for example at least 5 to 7 days, each day comprising at 1-10 administration events, such as for example two administration events, for example administration of one capsule in the morning and one in the evening.

The safety, tolerability and efficacy of autologous microbiota treatment is analyzed essentially as described in Example 2. The reconstitution of the microbiota is monitored, for example as microbiota profile in fecal samples obtained from the patient at different time points during and after completed treatment, as described in Examples 4-5.

Results:

It is expected that the microbiota is successfully reconstituted in the patients receiving autologous fecal samples, such as patients receiving capsules of autologous fecal samples. In particular, the reconstitution in said patients is expected to occur faster than in patients not receiving any treatment. Clinical outcomes, including stool frequency and consistency as well general and gastrointestinal well-being is expected to be significantly improved in patient receiving autologous fecal samples. Additionally, it is expected that a decrease of the number resistant bacteria will occur faster in patients receiving autologous fecal samples compared to patients not receiving any treatment

REFERENCES

1. Bartlett J G. Clinical practice. Antibiotic-associated diarrhea. N Engl J Med 2002; 346(5): 334-9.
2. Hensgens M P, Goorhuis A, Dekkers O M, van Benthem B H, Kuijper E J. All-cause and disease-specific mortality in hospitalized patients with *Clostridium difficile* infection: a multicenter cohort study. Clin Infect Dis 2013; 56(8): 1108-16.
3. Lessa F C, Mu Y, Bamberg W M, et al. Burden of *Clostridium difficile* infection in the United States. N Engl J Med 2015; 372(9): 825-34.
4. Mäkitalo B, Åkerlund T. *Clostridium difficile* rapport. Available at: http://www.folkhalsomyndigheten.se/amnesomraden/statistik-och-undersokningar/sjukdomsstatistik/*Clostridium-difficile*-infektion/. Accessed 20160127.
5. Garey K W, Sethi S, Yadav Y, DuPont H L. Meta-analysis to assess risk factors for recurrent *Clostridium difficile* infection. J Hosp Infect 2008; 70(4): 298-304.
6. Pepin J, Valiquette L, Gagnon S, Routhier S, Brazeau I. Outcomes of *Clostridium difficile*-associated disease treated with metronidazole or vancomycin before and after the emergence of NAP1/027. Am J Gastroenterol 2007; 102(12): 2781-8.
7. Vardakas K Z, Polyzos K A, Patouni K, Rafailidis P I, Samonis G, Falagas M E. Treatment failure and recurrence of *Clostridium difficile* infection following treatment with vancomycin or metronidazole: a systematic review of the evidence. Int J Antimicrob Agents 2012; 40(1): 1-8.
8. van Nood E, Vrieze A, Nieuwdorp M, et al. Duodenal infusion of donor feces for recurrent *Clostridium difficile*. N Engl J Med 2013; 368(5): 407-15.
9. Costello S P, Conlon M A, Vuaran M S, Roberts-Thomson I C, Andrews J M. Fecal microbiota transplant for recurrent *Clostridium difficile* infection using long-term frozen stool is effective: clinical efficacy and bacterial viability data. Aliment Pharmacol Ther 2015; 42(8): 1011-8.
10. Kelly C R, Ihunnah C, Fischer M, et al. Fecal microbiota transplant for treatment of *Clostridium difficile* infection in immunocompromised patients. Am J Gastroenterol 2014; 109(7): 1065-71.
11. Lee C H, Steiner T, Petrof E O, et al. Frozen vs Fresh Fecal Microbiota Transplantation and Clinical Resolution of Diarrhea in Patients With Recurrent *Clostridium difficile* Infection: A Randomized Clinical Trial. Jama 2016; 315(2): 142-9.
12. Youngster I, Russell G H, Pindar C, Ziv-Baran T, Sauk J, Hohmann E L. Oral, capsulized, frozen fecal microbiota transplantation for relapsing *Clostridium difficile* infection. Jama 2014; 312(17): 1772-8.
13. Youngster I, Sauk J, Pindar C, et al. Fecal microbiota transplant for relapsing *Clostridium difficile* infection using a frozen inoculum from unrelated donors: a randomized, open-label, controlled pilot study. Clin Infect Dis 2014; 58(11): 1515-22.
14. Blot S, Depuydt P, Vogelaers D, et al. Colonization status and appropriate antibiotic therapy for nosocomial bacteremia caused by antibiotic-resistant gram-negative bacteria in an intensive care unit. Infect Control Hosp Epidemiol 2005; 26(6): 575-9.
15. Caballero S, Carter R, Ke X, et al. Distinct but Spatially Overlapping Intestinal Niches for Vancomycin-Resistant *Enterococcus faecium* and Carbapenem-Resistant *Klebsiella pneumoniae*. PLoS Pathog 2015; 11(9): e1005132.
16. Donskey C J. The role of the intestinal tract as a reservoir and source for transmission of nosocomial pathogens. Clin Infect Dis 2004; 39(2): 219-26.
17. Trotti A, Colevas A D, Setser A, et al. CTCAE v3.0: development of a comprehensive grading system for the adverse effects of cancer treatment. Semin Radiat Oncol 2003; 13(3): 176-81.
18. Caporaso J G, Kuczynski J, Stombaugh J, et al. QIIME allows analysis of high-throughput community sequencing data. Nat Methods 2010; 7(5): 335-6.
19. Youngster I, Mahabamunuge J, Systrom H K, et al, Oral, frozen fecal microbiota transplant (FMT) capsules for recurrent *Clostridium difficile* infection, BMC Med 2016; 14 (1):134.

ITEMIZED LIST OF EMBODIMENTS

1. Autologous fecal sample, obtained from a subject and comprising at least one desired species of live microorganism, for use in the prevention and/or treatment of microbial dysbiosis in the gastrointestinal tract in said subject, wherein said use comprises 1-10 oral administration events per day during 1-30 days.
2. Autologous fecal sample for use according to item 1, wherein said at least one desired species of live microorganisms is present in the gastrointestinal tract of said subject when in a healthy condition.

3. Autologous fecal sample for use according to item 1 or 2, wherein said subject suffers from a chronic disease and said at least one desired species of live microorganisms is present in the gastrointestinal tract of said subject when in a state of remission.
4. Autologous fecal sample for use according to any one of items 1-3, wherein said sample is obtained from said subject while in said healthy condition or said state of remission.
5. Autologous fecal sample for use according to any one of items 1-4, wherein said sample comprising least one desired species of live microorganisms comprises the diversity of live microorganisms present in the gastrointestinal tract of said subject, such as the unselected diversity of live microorganisms present in the gastrointestinal tract of said subject.
6. Autologous fecal sample for use according to any one of items 1-5, wherein said diversity is specific to said subject.
7. Autologous fecal sample for use according to any one of items 1-6, wherein said diversity of live microorganisms comprises bacteria from at least one, such as at least two, such as at least three, such as four, of the phyla Firmicutes, Bacteroidetes, Actinobacteria and Proteobacteria.
8. Autologous fecal sample for use according to any one of items 1-7, wherein said diversity of live microorganisms comprises bacteria from at least one, such as at least two, such as at least three, such as at least four, such as at least five, such as at least six, such as at least seven, such as eight, of the genera *Bacteroides, Clostridium, Fecalibacterium, Eubacterium, Ruminococcus, Peptococcus, Peptostreptococcus* and *Bifidobacterium*.
9. Autologous fecal sample for use according to any one of items 1-8, wherein said prevention and/or treatment comprises autologous reconstitution of normal microbiota of the gastrointestinal tract, such as the normal microbiota downstream of the duodenum.
10. Autologous fecal sample for use according to item 9, wherein the autologous reconstitution comprises repopulation of the gastrointestinal tract with said at least one species of microorganisms, such as at least one species of bacteria.
11. Autologous fecal sample for use according to any one of items 1-10, wherein said microbial dysbiosis is caused by medical treatment.
12. Autologous fecal sample for use according to any one of items 1-11, wherein said medical treatment is antibiotic treatment.
13. Autologous fecal sample for use according to any one of items 1-11, wherein said medical treatment is selected from the group consisting of immunosuppressive treatment; cytostatic treatment; radiation treatment; surgical treatment; and treatment with biguanides, such as metformin.
14. Autologous fecal sample for use according to any one of items 1-13, wherein said medical treatment, is earlier medical treatment.
15. Autologous fecal sample for use according to any one of items 1-12 or 14, wherein said oral administration begins at least 1 day after completion of the antibiotic treatment, such as within 1-5 days, such as 1-4 days, such as 1-3 days, such as 1-2 days after the completion of the antibiotic treatment.
16. Autologous fecal sample for use according to any one of items 1-11 and 13, wherein said medical treatment, is concomitant medical treatment.
17. Autologous fecal sample for use according to any one of items 1-10, wherein said microbial dysbiosis is associated with a chronic disease affecting the gastrointestinal tract, such as a chronic disease selected from the group consisting of irritable bowel syndrome, Crohn's disease, ulcerative colitis, collagenous colitis and diverticulitis.
18. Autologous fecal sample for use according to any one of items 1-10, wherein said microbial dysbiosis is associated with an infectious disease affecting the gastrointestinal tract, such as an infectious disease selected from the group consisting of diseases caused by a bacterial infection, such as an infection by *Clostridium, Salmonella*, EHEC, ETEC, *Klebsiella* or *Shigella*; a viral infection, such as an infection by calicivirus or ROTA-virus; and a parasitic infection, such as an infection by *Crytosporidium* or *Giardia*.
19. Autologous fecal sample for use according to item 18, wherein said microbial dysbiosis is associated with a bacterial infection selected from the group consisting of infections by *Clostridium, Salmonella*, EHEC, ETEC, *Klebsiella* and *Shigella*.
20. Autologous fecal sample for use according to item 19, wherein said microbial dysbiosis is associated with a *Clostridium difficile* infection, such as an ongoing *Clostridium difficile* infection or an earlier *Clostridium difficile* infection.
21. Autologous fecal sample for use according to any one of items 18-20, wherein said prevention and/or treatment is carried out post at least one *Clostridium difficile* infection.
22. Autologous fecal sample for use according to any one of items 18-21, wherein said prevention is the prevention of occurrence or recurrence of a *Clostridium difficile* infection.
23. Autologous fecal sample for use according to any one of items 18-22, wherein said prevention is the prevention of *Clostridium difficile* translocation across the intestinal membrane.
24. Autologous fecal sample for use according to any one of items 19-23, wherein said oral administration begins at least 1 day after completion of an antibiotic treatment, such as within 1-5 days, such as 1-4 days, such as 1-3 days, such as 1-2 days after the completion of an antibiotic treatment of an infection, such as said *Clostridium difficile* infection.
25. Autologous fecal sample for use according to any one of items 1-24, wherein said administration comprises 1-8 administration events per day, such as 1-6 administration events per day, such as 2-6 administration events per day, such as 2-4 administration events per day, such as 2-3 administration events per day.
26. Autologous fecal sample for use according to any one of items 1-25, wherein said administration is continued for a period of at least 5 days, such as for 5-30 days, such as 5-14 days, such as 5-10 days, such as 5-7 days, such as 5, 6 or 7 days.
27. Autologous fecal sample for use according to any one of items 1-26, wherein administration is oral self-administration, such as oral out-patient self-administration.
28. Pharmaceutical composition for oral administration comprising a therapeutically effective amount of an autologous fecal sample, obtained from a subject and comprising at least one desired species of live microorganisms, and at least one pharmaceutically acceptable excipient, for use in the prevention and/or treatment of microbial dysbiosis in the gastrointestinal tract of said subject, wherein said use comprises 1-10 administration events per day during 1-30 days.

29. Pharmaceutical composition for use according to item 28, wherein said at least one desired species of live microorganism is present in the gastrointestinal tract of said subject when in a healthy condition.
30. Pharmaceutical composition for use according to item 28 or 29, wherein said subject suffers from a chronic disease and said at least one desired species of live microorganisms is present in the gastrointestinal tract of said subject when in a state of remission.
31. Pharmaceutical composition for use according to any one of items 28-30, wherein said sample is obtained from said subject while in said healthy condition or said state of remission.
32. Pharmaceutical composition for use according to any one of items 28-31, wherein said sample comprising least one desired species of live microorganisms comprises the diversity of live microorganisms present in the gastrointestinal tract of said subject, such the unselected diversity of live bacteria present in the gastrointestinal tract of said subject.
33. Pharmaceutical composition for use according to any one of items 28-32, wherein said diversity is specific to said subject.
34. Pharmaceutical composition for use according to any one of items 28-33, wherein said diversity of live microorganisms comprises bacteria from at least one, such as at least two, such as at least three, such as four, of the phyla Firmicutes, Bacteroidetes, Actinobacteria and Proteobacteria.
35. Pharmaceutical composition for use according to any one of items 28-34, wherein said diversity of live microorganisms comprises bacteria from at least one, such as at least two, such as at least three, such as at least four, such as at least five, such as at least six, such as at least seven, such as eight, of the genera *Bacteroides, Clostridium, Fecalibacterium, Eubacterium, Ruminococcus, Peptococcus, Peptostreptococcus*, and *Bifidobacterium*.
36. Pharmaceutical composition for use according to item 28-35, wherein said prevention and/or treatment comprises autologous reconstitution of normal microbiota of the gastrointestinal tract, such as the normal microbiota downstream of the duodenum.
37. Pharmaceutical composition for use according to item 28-36, wherein the autologous reconstitution comprises repopulation of the gastrointestinal tract with at least one desired species of microorganisms.
38. Pharmaceutical composition for use according to any one of items 28-37, wherein said microbial dysbiosis is caused by medical treatment.
39. Pharmaceutical composition for use according to any one of items 28-38, wherein said medical treatment is antibiotic treatment.
40 Pharmaceutical composition for use according to any one of items 28-38, wherein said medical treatment is selected from the group consisting of immunosuppressive treatment; cytostatic treatment; radiation treatment; surgical treatment; and treatment with biguanides, such as metformin.
41. Pharmaceutical composition for use according to item 28-40, wherein said medical treatment is earlier medical treatment.
42. Pharmaceutical composition for use according to any one of items 28-39 or 41, wherein said oral administration begins at least 1 day after completion of the antibiotic treatment, such as within 1-5 days, such as 1-4 days, such as 1-3 days, such as 1-2 days after the completion of the antibiotic treatment.
43. Pharmaceutical composition for use according to any one of items 28-38 and 40, wherein said medical treatment is concomitant medical treatment.
44. Pharmaceutical composition for use according to any one of items 28-37, wherein said microbial dysbiosis is associated with a chronic disease affecting the gastrointestinal tract, such as a chronic disease selected from the group consisting of irritable bowel syndrome, Crohn's disease, ulcerative colitis, collagenous colitis and diverticulitis.
45. Pharmaceutical composition for use according to any one of items 28-37, wherein said microbial dysbiosis is associated with an infectious disease affecting the gastrointestinal tract selected from the group consisting of a disease caused by a bacterial infection, such as an infection by *Clostridium, Salmonella*, EHEC, ETEC, *Klebsiella* or *Shigella*; a viral infection, such as an infection by calicivirus or ROTA-virus; and a parasitic infection, such as an infection by *Crytosporidium* or *Giardia*.
46. Pharmaceutical composition for use according to item 45, wherein said microbial dysbiosis is associated with a bacterial infection selected from the group consisting of infections by *Clostridium, Salmonella*, EHEC, ETEC, *Klebsiella* and *Shigella*.
47. Pharmaceutical composition for use according to item 46, wherein said microbial dysbiosis is associated with a *Clostridium difficile* infection, such as an ongoing *Clostridium difficile* infection or an earlier *Clostridium difficile* infection.
48. Pharmaceutical composition for use according to any one of items 45-47, wherein said prevention and/or treatment is carried out post at least one *Clostridium difficile* infection.
49. Pharmaceutical composition for use according to any one of items 45-48, wherein said prevention is the prevention of occurrence or recurrence of a *Clostridium difficile* infection.
50. Pharmaceutical composition for use according to any one of items 45-49, wherein said prevention is the prevention of *Clostridium difficile* translocation across the intestinal membrane.
51. Pharmaceutical composition for use according to any one of items 46-50, wherein said oral administration begins at least 1 day after completion of an antibiotic treatment, such as within 1-5 days, such as 1-4 days, such as 1-3 days, such as 1-2 days after the completion of an antibiotic treatment of an infection, such as of said *Clostridium difficile* infection.
52. Pharmaceutical composition for use according to any one of items 28-51, wherein said therapeutically effective amount is at least $1 \times 10^7$ CFU, such as at least $1 \times 10^8$ CFU, such as at least $1 \times 10^9$ CFU, such as at least $1 \times 10^{10}$ CFU of said microorganisms per administration event.
53. Pharmaceutical composition for use according to any one of items 28-52, which is stable at 4-10° C., such as 4-8° C., or at ≤−20° C., or at −70° C. for a period of at least 10 days, such as at least 30 days, such as at least 60 days.
54. Pharmaceutical composition for use according to any one of items 28-53, which comprises at least $1 \times 10^7$ CFU, such as at least $1 \times 10^8$ CFU of said live microorganisms after at least 10 days of storage at 4-10° C., such as 4-8° C., or at −20° C., or at ≤−70° C.
55. Pharmaceutical composition for use according to any one of items 28-44, wherein said administration comprises 1-8 administration events per day, such as 1-6 administration events per day, such as 2-6 administration 56. Pharmaceutical composition for use according to any one of items 28-55, wherein said administration is continued for a period of at least 5 days, such as for 5-30 days, such as 5-14 days, such as 5-10 days, such as 5-7 days, such as 5, 6 or 7 days.
57. Pharmaceutical composition for use according to any one of items 28-56, is formulated for oral self-administration, such as out-patient oral self-administration.
58. Pharmaceutical composition for use according to any one of items 28-57, which is formulated as a capsule, a pill, or a tablet, such as a capsule or tablet, such as an enteric resistant capsule or tablet.
59. Method for prevention and/or treatment of microbial dysbiosis in the gastrointestinal tract, comprising orally administering to a subject in need thereof a therapeutically effective amount of an autologous fecal sample as defined in any one of items 1-8 or a pharmaceutical composition as defined in any one of items 28-35 and 52-58, wherein said method comprises 1-10 administration events per day during 1-30 days.
60. Method according to item 59, wherein said prevention and/or treatment comprises autologous reconstitution of normal microbiota of the gastrointestinal tract, such as the normal microbiota downstream of the duodenum.
61. Method according to item 60, wherein the autologous reconstitution comprises repopulation of the gastrointestinal tract with at least one species of microorganisms, such as at least one species of bacteria.
62. Method according to any one of items 59-61, wherein said microbial dysbiosis is caused by medical treatment.
63. Method according to any one of items 59-62, wherein said medical treatment is antibiotic treatment.
64. Method according to any one of items 57-62, wherein said medical treatment is selected from the group consisting of immunosuppressive treatment; cytostatic treatment; radiation treatment; surgical treatment; and treatment with biguanides, such as metformin.
65. Method according to any one of items 57-64, wherein said medical treatment is earlier medical treatment.
66. Method according to any one of items 57-63 or 65, wherein said oral administration begins at least 1 day after completion of the antibiotic treatment, such as within 1-5 days, such as 1-4 days, such as 1-3 days, such as 1-2 days after the completion of the antibiotic treatment.
67. Method according to any one of items 57-62 and 64, wherein said medical treatment is concomitant medical treatment.
68. Method according to any one of items 57-56, wherein said microbial dysbiosis is associated with an infectious disease affecting the gastrointestinal tract selected from the group consisting of disease caused by a bacterial infection, such as an infection by *Clostridium, Salmonella*, EHEC, ETEC, *Klebsiella* or *Shigella*; a viral infection, such as an infection by calicivirus or ROTA-virus; and a parasitic infection, such as an infection by *Crytosporidium* or *Giardia*.
69. Method according to item 68, wherein said microbial dysbiosis is associated with a bacterial infection selected from the group consisting of infections by *Clostridium, Salmonella*, EHEC, ETEC, *Klebsiella* and *Shigella*.
70. Method according to item 69, wherein said microbial dysbiosis is associated with a *Clostridium difficile* infection, such as an ongoing *Clostridium difficile* infection or an earlier *Clostridium difficile* infection.
71. Method according to any one of items 8-70, wherein said prevention and/or treatment is carried out post at least one *Clostridium difficile* infection.
72. Method according to any one of items 68-71, wherein said prevention is the prevention of occurrence or recurrence of a *Clostridium difficile* infection.
73. Method according to any one of items 68-72, wherein said prevention is the prevention of *Clostridium difficile* translocation across the intestinal membrane.
74. Method according to any one of items 69-73, wherein said oral administration begins at least 1 day after completion of an antibiotic treatment, such as within 1-5 days, such as 1-4 days, such as 1-3 days, such as 1-2 days after the completion of an antibiotic treatment of said infection, such as said *Clostridium difficile* infection.
75. Method according to any one of items 57-4 wherein said administration is oral self-administration.
76. Method according to any one of items 57-75, wherein said oral administration is out-patient oral self-administration.
77. Method according to any one of items 57-76, wherein said administration comprises 1-8 administration events per day, such as 1-6 administration events per day, such as 2-6 administration events per day, such as 2-4 times per day, such as 2-3 administration events per day.
78. Method according to any one of items 57-77, wherein said administration is carried out for a period of at least 5 days, such as for 5-30 days, such as 5-14 days, such as 5-10 days, such as 5-7 days, such as 5, 6 or 7 days.
79. Method according to any one of items 57-78, further comprising administration of an additional therapeutic agent.
80. Kit comprising i) an autologous fecal sample as defined in any one of items 1-8 or a pharmaceutical composition as defined in any one of items 28-35 and 52-58 and ii) an additional therapeutic agent.
81. Kit according to item 80, wherein said additional therapeutic agent is an immunosuppressive agent.
82. Kit according to any one of items 80-81, wherein said additional therapeutic agent is formulated for oral, subcutaneous, intramuscular or intravenous administration, such as oral or intravenous administration.
83. Kit comprising i) an autologous fecal sample as defined in any one of items 1-8 or a pharmaceutical composition as defined in any one of items 28-35 and 52-58 and ii) an additional agent effective to promote bacterial repopulation.
84. Kit according to any one of items 80-83, wherein said autologous fecal sample and said additional agent are formulated for concomitant or simultaneous administration.
85. Kit according to item 84, wherein said sample and agent are formulated for concomitant administration within less than 48 hours of each other, such as within less than 24 hours, such as within less than 12 hours, such as within less than 6 hours.
86. Kit comprising a) at least one oral capsule comprising an autologous fecal sample as defined in any one of items 1-8 or a pharmaceutical composition as defined in any one of items 28-35 and 52-58 and b) at least one corresponding oral capsule which does not comprise any therapeutically active agent.
87. Use of an autologous fecal sample as defined in any one of items 1-27, for the manufacture of a medicament for the prevention and/or treatment of microbial dysbiosis in the gastrointestinal tract of a subject in need thereof.

The invention claimed is:

1. A method for prevention and/or treatment of microbial dysbiosis in the gastrointestinal tract comprising orally administering to a subject in need thereof a therapeutically effective amount of an autologous fecal sample which comprises at least one desired species of live microorganisms, wherein said method comprises 1-10 oral administration events per day during 2-30 days, wherein said sample is obtained from said subject while in healthy condition or a state of remission and wherein said sample comprises the unselected diversity of live microorganisms of the gastrointestinal tract of said subject.

2. The method for prevention and/or treatment of microbial dysbiosis according to claim 1, wherein said at least one desired species of live microorganisms is present in the gastrointestinal tract of said subject when in a healthy condition or, wherein said at least one desired species of live microorganisms is present in the gastrointestinal tract of said subject when in a state of remission in the case said subject suffers from a chronic disease.

3. The method for prevention and/or treatment of microbial dysbiosis according to claim 1, wherein said prevention and/or treatment comprises autologous reconstitution of normal microbiota of the gastrointestinal tract.

4. The method for prevention and/or treatment of microbial dysbiosis according to claim 1, wherein said microbial dysbiosis is caused by medical treatment.

5. The method for prevention and/or treatment of microbial dysbiosis according to claim 4, wherein said medical treatment is antibiotic treatment.

6. The method prevention and/or treatment of microbial dysbiosis according to claim 4, wherein said medical treatment is selected from the group consisting of immunosuppressive treatment; cytostatic treatment; radiation treatment; surgical treatment; and treatment with biguanides.

7. The method for prevention and/or treatment of microbial dysbiosis according to claim 4, wherein said medical treatment, is an earlier medical treatment.

8. The method for prevention and/or treatment of microbial dysbiosis according to claim 5, wherein said oral administration begins at least 1 day after completion of the antibiotic treatment.

9. The method for prevention and/or treatment of microbial dysbiosis according to claim 1, wherein said microbial dysbiosis is associated with a disease selected from the group consisting of chronic diseases affecting the gastrointestinal tract and infectious diseases affecting the gastrointestinal tract.

10. The method for prevention and/or treatment of microbial dysbiosis according to claim 1, wherein said microbial dysbiosis is associated with an infectious disease selected from the group consisting of infection by *Clostridium*, *Salmonella*, EHEC, ETEC, *Klebsiella* or *Shigella*; infection by calicivirus or ROTA-virus; and infection by *Crytosporidium* or *Giardia*.

11. The method for prevention and/or treatment of microbial dysbiosis according to claim 1, wherein said administration is continued for a period of at least 5 days.

12. The method for prevention and/or treatment of microbial dysbiosis according to claim 1, wherein said prevention and/or treatment comprises autologous reconstitution of normal microbiota downstream of the duodenum and wherein the autologous reconstitution comprises repopulation of the gastrointestinal tract downstream of the duodenum with said at least one desired species of live microorganisms.

13. The method for prevention and/or treatment of microbial dysbiosis according to claim 1, wherein said microbial dysbiosis is associated with an infectious disease affecting the gastrointestinal tract caused by a bacterial infection by *Clostridium*.

* * * * *